US 011801342B2

(12) United States Patent
Lacy et al.

(10) Patent No.: US 11,801,342 B2
(45) Date of Patent: Oct. 31, 2023

(54) HOUSING ARRANGEMENTS FOR INFUSION PUMPS

(71) Applicant: Smiths Medical ASD, Inc., Plymouth, MN (US)

(72) Inventors: Christopher Allen Lacy, Arden Hills, MN (US); Grant A. Adams, Anoka, MN (US); Steven Plager, Eden Prairie, MN (US); Kevin Krautbauer, St. Paul, MN (US); Jonathan Sanborn, St. Louis Park, MN (US); Manfred Maiers, Savage, MN (US); Walter Dobrovolny, St. Paul, MN (US); Eric Wilkowske, North Oaks, MN (US)

(73) Assignee: Smiths Medical ASD, Inc., Plymouth, MN (US)

( * ) Notice: Subject to any disclaimer, the term of this patent is extended or adjusted under 35 U.S.C. 154(b) by 876 days.

(21) Appl. No.: 16/627,949

(22) PCT Filed: Jul. 19, 2018

(86) PCT No.: PCT/US2018/042907
§ 371 (c)(1),
(2) Date: Dec. 31, 2019

(87) PCT Pub. No.: WO2019/018658
PCT Pub. Date: Jan. 24, 2019

(65) Prior Publication Data
US 2020/0129691 A1 Apr. 30, 2020

Related U.S. Application Data

(60) Provisional application No. 62/534,407, filed on Jul. 19, 2017.

(51) Int. Cl.
A61M 5/145 (2006.01)

(52) U.S. Cl.
CPC ..... *A61M 5/1456* (2013.01); *A61M 2205/123* (2013.01); *A61M 2205/3584* (2013.01);
(Continued)

(58) Field of Classification Search
None
See application file for complete search history.

(56) References Cited

U.S. PATENT DOCUMENTS 3,778,195 A 12/1973 Bamberg
4,537,561 A 8/1985 Xanthopoulos
(Continued)

FOREIGN PATENT DOCUMENTS

AU 2009348770 B2 4/2015
AU 2010208446 B2 9/2015
(Continued)

OTHER PUBLICATIONS

US 9,222,472 B2, 12/2015, Gray et al. (withdrawn)
(Continued)

*Primary Examiner* — Manuel A Mendez
(74) *Attorney, Agent, or Firm* — Patterson Thuente IP

(57) ABSTRACT

An infusion pump, including a housing, a user interface, a motor and a set of drive components, and a controller. The housing enables selective stacked attachment with other infusion pumps. The housing includes a top portion with a handle integrated into an outer surface that partially defines a generally U-shaped retaining feature. The housing also includes a bottom portion with a generally U-shaped projection that is contoured to selectively mate with the retaining feature of another infusion pump. The user interface provides a front side to the housing that receives commands regarding infusion pump operation. The motor and set of drive components are at least partially located within the housing and mechanically direct infusion of infusate. The
(Continued)

controller is located within the housing and that controls operation of the motor and the set of drive components.

18 Claims, 18 Drawing Sheets

(52) U.S. Cl.
CPC ............... *A61M 2205/505* (2013.01); *A61M 2205/8206* (2013.01)

(56) References Cited

U.S. PATENT DOCUMENTS

| | | | |
|---|---|---|---|
| 4,620,736 A | 11/1986 | Shanks | |
| 4,749,109 A | 6/1988 | Kamen | |
| 4,756,706 A * | 7/1988 | Kerns | A61M 5/142 |
| | | | 128/DIG. 13 |
| 4,978,335 A | 12/1990 | Arthur, III | |
| 5,034,004 A | 7/1991 | Crankshaw | |
| D328,952 S | 8/1992 | Arioka | |
| 5,236,416 A | 8/1993 | McDaniel et al. | |
| 5,254,096 A | 10/1993 | Rondelet et al. | |
| D344,684 S | 3/1994 | Metz et al. | |
| 5,295,966 A | 3/1994 | Stem et al. | |
| D348,101 S | 6/1994 | Poli et al. | |
| 5,364,364 A | 11/1994 | Kasvikis et al. | |
| 5,425,173 A | 6/1995 | Moss et al. | |
| D360,259 S | 7/1995 | Ijiri et al. | |
| 5,431,509 A | 7/1995 | Anderson et al. | |
| 5,452,807 A | 9/1995 | Foster et al. | |
| D363,468 S | 10/1995 | Mieki et al. | |
| 5,478,211 A | 12/1995 | Dominiak et al. | |
| D367,527 S | 2/1996 | Marston et al. | |
| D367,528 S | 2/1996 | Marston et al. | |
| D371,194 S | 6/1996 | Marston et al. | |
| 5,533,981 A | 7/1996 | Mandro et al. | |
| 5,545,140 A | 8/1996 | Conero et al. | |
| 5,551,850 A | 9/1996 | Williamson et al. | |
| 5,601,420 A | 2/1997 | Warner et al. | |
| 5,620,312 A | 4/1997 | Hyman et al. | |
| 5,647,491 A | 7/1997 | Foster et al. | |
| 5,647,854 A | 7/1997 | Olsen et al. | |
| D390,654 S | 2/1998 | Alsberg et al. | |
| 5,782,805 A | 7/1998 | Meinzer et al. | |
| 5,807,322 A | 9/1998 | Lindsey et al. | |
| 5,814,009 A | 9/1998 | Wheatman | |
| 5,814,015 A | 9/1998 | Gargano et al. | |
| 5,823,746 A | 10/1998 | Johnson | |
| 5,840,058 A | 11/1998 | Ammann et al. | |
| 5,879,360 A | 3/1999 | Crankshaw | |
| 5,901,150 A | 5/1999 | Jhuboo et al. | |
| 5,904,668 A | 5/1999 | Hyman et al. | |
| 5,954,485 A | 9/1999 | Johnson et al. | |
| 5,954,527 A | 9/1999 | Jhuboo et al. | |
| 6,019,745 A | 2/2000 | Gray | |
| D435,021 S | 12/2000 | Davis et al. | |
| 6,187,400 B1 | 2/2001 | Woo et al. | |
| 6,195,887 B1 | 3/2001 | Danby et al. | |
| 6,203,528 B1 | 3/2001 | Deckert et al. | |
| 6,213,723 B1 | 4/2001 | Danby et al. | |
| 6,213,739 B1 | 4/2001 | Phallen et al. | |
| 6,231,320 B1 | 5/2001 | Lawless et al. | |
| 6,312,227 B1 | 11/2001 | Davis | |
| D455,489 S | 4/2002 | Beck et al. | |
| 6,407,335 B1 | 6/2002 | Franklin-Lees et al. | |
| 6,500,151 B1 | 12/2002 | Cobb et al. | |
| 6,519,569 B1 | 2/2003 | White et al. | |
| 6,551,277 B1 | 4/2003 | Ford | |
| D474,837 S | 5/2003 | Gillespie, Jr. et al. | |
| 6,575,936 B1 | 6/2003 | Kojima et al. | |
| 6,592,551 B1 | 7/2003 | Cobb | |
| 6,593,528 B2 | 7/2003 | Franklin-Lees et al. | |
| 6,656,148 B2 | 12/2003 | Das et al. | |
| 6,659,976 B2 | 12/2003 | Beck et al. | |
| 6,722,865 B2 | 4/2004 | Domroese | |
| 6,742,992 B2 | 6/2004 | Davis | |
| 6,743,202 B2 | 6/2004 | Hirschman et al. | |
| D501,924 S | 2/2005 | Cise et al. | |
| 6,852,094 B2 | 2/2005 | Beck et al. | |
| D504,507 S | 4/2005 | Ziegler et al. | |
| D507,647 S | 7/2005 | Beck et al. | |
| 6,966,895 B2 | 11/2005 | Tribe | |
| D523,553 S | 6/2006 | Beck et al. | |
| 7,121,815 B2 | 10/2006 | Knuth et al. | |
| 7,160,087 B2 | 1/2007 | Fathallah et al. | |
| 7,161,488 B2 | 1/2007 | Frasch | |
| D536,783 S | 2/2007 | Cise et al. | |
| 7,211,726 B2 | 5/2007 | Bally et al. | |
| 7,214,038 B2 | 5/2007 | Saxer et al. | |
| 7,227,081 B2 | 6/2007 | Bally et al. | |
| 7,236,936 B2 | 6/2007 | White et al. | |
| 7,273,359 B2 | 9/2007 | Blight et al. | |
| 7,278,615 B2 | 10/2007 | Schubert et al. | |
| 7,356,382 B2 | 4/2008 | Vanderveen | |
| 7,422,570 B2 | 9/2008 | Gerlach et al. | |
| D586,463 S | 2/2009 | Evans et al. | |
| D586,468 S | 2/2009 | Petersen | |
| 7,503,808 B1 * | 3/2009 | O'Shea | H01R 31/065 |
| | | | 439/639 |
| 7,553,291 B2 | 6/2009 | Duffy et al. | |
| 7,556,616 B2 | 7/2009 | Fathallah et al. | |
| 7,632,079 B2 | 12/2009 | Hershberger et al. | |
| 7,635,349 B2 | 12/2009 | Tribe et al. | |
| D626,647 S | 11/2010 | Amborn et al. | |
| 7,859,473 B2 | 12/2010 | Gibson | |
| 7,884,735 B2 | 2/2011 | Newkirk | |
| 7,896,572 B2 | 3/2011 | Fathallah et al. | |
| 7,934,912 B2 | 5/2011 | Voltenburg, Jr. et al. | |
| 7,963,797 B2 | 6/2011 | Knappe | |
| 7,967,773 B2 | 6/2011 | Amborn et al. | |
| D642,677 S | 8/2011 | Boaz | |
| 8,062,008 B2 | 11/2011 | Voltenburg, Jr. et al. | |
| 8,083,503 B2 | 12/2011 | Voltenburg, Jr. et al. | |
| 8,109,906 B2 | 2/2012 | Smisson, III et al. | |
| D655,810 S | 3/2012 | Amborn et al. | |
| 8,161,810 B2 | 4/2012 | Cadieux et al. | |
| 8,182,461 B2 | 5/2012 | Pope et al. | |
| D669,096 S | 10/2012 | Katsura | |
| 8,337,168 B2 | 12/2012 | Rotem et al. | |
| 8,388,582 B2 | 3/2013 | Eubanks et al. | |
| 8,388,598 B2 | 3/2013 | Steinkogler | |
| D679,379 S | 4/2013 | Katsura | |
| 8,430,849 B2 | 4/2013 | Smith et al. | |
| 8,459,968 B2 | 6/2013 | Juretich et al. | |
| 8,496,613 B2 | 7/2013 | Zhou | |
| 8,499,108 B2 | 7/2013 | Edwards et al. | |
| D691,259 S | 10/2013 | Estes et al. | |
| 8,545,458 B2 | 10/2013 | Gagliardoni et al. | |
| 8,551,056 B2 | 10/2013 | Gagliardoni et al. | |
| 8,551,057 B2 | 10/2013 | Gagliardoni et al. | |
| 8,662,458 B2 | 3/2014 | Henault et al. | |
| 8,715,224 B2 | 5/2014 | Kamen et al. | |
| 8,777,590 B2 | 7/2014 | Moy et al. | |
| 8,834,443 B2 | 9/2014 | Yeung | |
| 8,859,972 B2 | 10/2014 | Cummings et al. | |
| 8,876,793 B2 | 11/2014 | Ledford et al. | |
| 8,911,403 B2 | 12/2014 | Flachbart et al. | |
| 8,974,415 B2 | 3/2015 | Robert et al. | |
| 8,986,252 B2 | 3/2015 | Cummings et al. | |
| 9,008,803 B2 | 4/2015 | Blomquist | |
| 9,011,379 B2 | 4/2015 | Hariharesan et al. | |
| D730,514 S | 5/2015 | Boaz et al. | |
| 9,050,411 B2 | 6/2015 | Kelly et al. | |
| 9,056,166 B2 | 6/2015 | Zhu | |
| 9,072,540 B2 | 7/2015 | Jamagin et al. | |
| 9,084,848 B2 | 7/2015 | Schiltges et al. | |
| 9,101,712 B2 | 8/2015 | Denis et al. | |
| 9,114,213 B2 | 8/2015 | Murakami et al. | |
| 9,115,708 B2 | 8/2015 | van der Merwe et al. | |
| 9,115,709 B2 | 8/2015 | Gray et al. | |
| 9,132,227 B2 | 9/2015 | Bryant, Jr. et al. | |
| 9,132,234 B2 | 9/2015 | Estes et al. | |
| 9,138,526 B2 | 9/2015 | Ware et al. | |
| 9,155,825 B2 | 10/2015 | Kelly et al. | |

(56) References Cited

U.S. PATENT DOCUMENTS

| | | |
|---|---|---|
| 9,155,835 B2 | 10/2015 | Watanabe et al. |
| 9,162,027 B2 | 10/2015 | Kamen et al. |
| 9,168,333 B2 | 10/2015 | Kelly et al. |
| 9,183,603 B2 | 11/2015 | Borges et al. |
| 9,192,711 B2 | 11/2015 | Barnes |
| 9,192,714 B2 | 11/2015 | Kaufmann et al. |
| 9,205,188 B2 | 12/2015 | Lanigan et al. |
| 9,238,101 B2 | 1/2016 | Hariharesan et al. |
| 9,242,035 B2 | 1/2016 | Karoor |
| 9,248,225 B2 | 2/2016 | Demers et al. |
| 9,248,230 B2 | 2/2016 | Geipel et al. |
| 9,265,879 B2 | 2/2016 | Gray |
| 9,265,890 B2 | 2/2016 | Chattaraj et al. |
| 9,272,089 B2 | 3/2016 | Jacobson et al. |
| 9,272,129 B2 | 3/2016 | Howlett et al. |
| 9,278,174 B2 | 3/2016 | Gray |
| 9,283,312 B2 | 3/2016 | Childers et al. |
| 9,283,370 B2 | 3/2016 | Travis et al. |
| 9,289,552 B2 | 3/2016 | Gerlach et al. |
| 9,295,778 B2 | 3/2016 | Kamen et al. |
| 9,302,039 B2 | 4/2016 | Kelly et al. |
| 9,314,566 B2 | 4/2016 | Wenger et al. |
| 9,320,849 B2 | 4/2016 | Smith et al. |
| 9,320,858 B2 | 4/2016 | Grimm et al. |
| 9,339,603 B2 | 5/2016 | Gray et al. |
| 9,352,083 B2 | 5/2016 | Heitmeiter et al. |
| 9,358,332 B2 | 6/2016 | McGill et al. |
| 9,359,885 B2 | 6/2016 | Slepicka et al. |
| 9,377,513 B2 | 6/2016 | Lindegger |
| 9,378,334 B2 | 6/2016 | Lee et al. |
| D761,741 S | 7/2016 | Santiago et al. |
| 9,387,286 B2 | 7/2016 | Kelly et al. |
| 9,415,150 B2 | 8/2016 | Hogard et al. |
| 9,421,313 B2 | 8/2016 | Kelly et al. |
| 9,427,520 B2 | 8/2016 | Batch et al. |
| 9,427,521 B2 | 8/2016 | Pope et al. |
| D765,832 S | 9/2016 | Hochman et al. |
| D766,204 S | 9/2016 | Takahata |
| 9,446,186 B2 | 9/2016 | Estes |
| 9,446,188 B2 | 9/2016 | Grant et al. |
| 9,468,713 B2 | 10/2016 | Hoenninger, III |
| 9,488,167 B2 | 11/2016 | Gray et al. |
| 9,498,573 B2 | 11/2016 | Smith et al. |
| 9,526,830 B2 | 12/2016 | Kamen et al. |
| 9,530,087 B2 | 12/2016 | Borges et al. |
| D777,119 S | 1/2017 | Lin et al. |
| 9,539,383 B2 | 1/2017 | Kohlbrecher |
| 9,545,475 B2 | 1/2017 | Borges et al. |
| 9,550,020 B2 | 1/2017 | Kelly et al. |
| 9,554,967 B2 | 1/2017 | Moi et al. |
| 9,561,324 B2 | 2/2017 | Estes |
| 9,572,919 B2 | 2/2017 | Kelly et al. |
| 9,572,923 B2 | 2/2017 | Howard et al. |
| 9,586,003 B2 | 3/2017 | Lee et al. |
| 9,592,338 B2 | 3/2017 | Pearson et al. |
| 9,593,679 B2 | 3/2017 | Gray et al. |
| 9,616,170 B2 | 4/2017 | Nakanishi et al. |
| 9,623,180 B2 | 4/2017 | Iio et al. |
| 9,623,198 B2 | 4/2017 | Kamen et al. |
| D787,504 S | 5/2017 | Hillman et al. |
| 9,642,965 B2 | 5/2017 | Marshall et al. |
| 9,649,431 B2 | 5/2017 | Gray et al. |
| 9,649,433 B2 | 5/2017 | Lanier, Jr. et al. |
| 9,656,052 B2 | 5/2017 | Slepicka et al. |
| 9,662,437 B2 | 5/2017 | Moosai |
| 9,662,438 B2 | 5/2017 | Kamen et al. |
| 9,669,161 B2 | 6/2017 | Bryant, Jr. et al. |
| 9,682,191 B2 | 6/2017 | Zhu |
| 9,682,199 B2 | 6/2017 | Walsh et al. |
| 9,690,909 B2 | 6/2017 | Stewart et al. |
| D791,937 S | 7/2017 | Schoenig et al. |
| 9,707,336 B2 | 7/2017 | Dang et al. |
| D793,346 S | 8/2017 | Folk et al. |
| 9,724,456 B2 | 8/2017 | Muller et al. |
| 9,724,458 B2 | 8/2017 | Grant et al. |
| 9,731,072 B2 | 8/2017 | Estes |
| 9,744,304 B2 | 8/2017 | Swift et al. |
| 9,753,015 B2 | 9/2017 | Bardina et al. |
| D800,717 S | 10/2017 | Hillman et al. |
| D801,519 S | 10/2017 | Sabin et al. |
| 9,775,964 B2 | 10/2017 | Eubanks et al. |
| 9,789,247 B2 | 10/2017 | Kamen et al. |
| 9,789,251 B2 | 10/2017 | Robert et al. |
| 9,795,729 B2 | 10/2017 | Childers et al. |
| D803,386 S | 11/2017 | Sabin et al. |
| D803,387 S | 11/2017 | Bodwell et al. |
| 9,808,316 B2 | 11/2017 | Hasegawa |
| 9,821,151 B2 | 11/2017 | Juretich et al. |
| 9,839,743 B2 | 12/2017 | Lanigan et al. |
| 9,839,745 B2 | 12/2017 | Paul et al. |
| 9,839,775 B2 | 12/2017 | McGill et al. |
| 9,839,776 B2 | 12/2017 | Helmore et al. |
| 9,849,235 B2 | 12/2017 | Mandro et al. |
| 9,861,732 B2 | 1/2018 | Scarpaci et al. |
| 9,861,740 B2 | 1/2018 | Adams |
| 9,872,950 B2 | 1/2018 | Kelly et al. |
| D810,958 S | 2/2018 | Lacy et al. |
| 9,886,550 B2 | 2/2018 | Lee et al. |
| 9,895,488 B2 | 2/2018 | Morton |
| D812,218 S | 3/2018 | Lacy et al. |
| 9,907,943 B2 | 3/2018 | Grant et al. |
| 9,925,315 B2 | 3/2018 | Eubanks et al. |
| 9,931,461 B2 | 4/2018 | Kamen et al. |
| 9,932,977 B2 | 4/2018 | Bresina et al. |
| 9,943,653 B2 | 4/2018 | Kamen et al. |
| 9,968,739 B2 | 5/2018 | Zollinger et al. |
| 9,976,551 B2 | 5/2018 | Blomquist |
| 9,987,410 B2 | 6/2018 | Helmore et al. |
| 9,993,600 B2 | 6/2018 | Lanier, Jr. et al. |
| 10,004,847 B2 | 6/2018 | Wander et al. |
| D823,456 S | 7/2018 | Lacy et al. |
| 10,022,494 B2 | 7/2018 | Shimizu |
| D828,547 S | 9/2018 | Lacy et al. |
| 10,076,608 B2 | 9/2018 | Dowden et al. |
| D830,546 S | 10/2018 | Lacy et al. |
| D840,021 S | 2/2019 | Lacy et al. |
| D846,735 S | 4/2019 | Sanborn et al. |
| D870,263 S | 12/2019 | Adams et al. |
| D871,572 S | 12/2019 | Lacy et al. |
| 2001/0013437 A1* | 8/2001 | Husted .............. A61G 5/1089 180/68.5 |
| 2001/0044602 A1 | 11/2001 | Angersbach et al. |
| 2002/0107476 A1 | 8/2002 | Mann et al. |
| 2002/0134570 A1 | 9/2002 | Franklin-Lees et al. |
| 2003/0060765 A1 | 3/2003 | Campbell et al. |
| 2003/0161744 A1 | 8/2003 | Vilks et al. |
| 2003/0214412 A1 | 11/2003 | Ho et al. |
| 2004/0057855 A1 | 3/2004 | Gerlach et al. |
| 2004/0167464 A1 | 8/2004 | Ireland et al. |
| 2004/0220526 A1 | 11/2004 | Boyne-Aitken |
| 2006/0129110 A1 | 6/2006 | Smith et al. |
| 2006/0184121 A1 | 8/2006 | Brockman et al. |
| 2006/0229577 A1 | 10/2006 | Roe et al. |
| 2007/0073236 A1 | 3/2007 | Mernoe et al. |
| 2007/0074596 A1 | 4/2007 | Siefert |
| 2007/0088249 A1 | 4/2007 | Duffy et al. |
| 2007/0167912 A1 | 7/2007 | Causey et al. |
| 2007/0179444 A1 | 8/2007 | Causey et al. |
| 2008/0103375 A1 | 5/2008 | Kiani |
| 2008/0200870 A1 | 8/2008 | Palmroos et al. |
| 2008/0281168 A1 | 11/2008 | Gibson et al. |
| 2008/0294140 A1 | 11/2008 | Patel et al. |
| 2008/0306437 A1* | 12/2008 | Jacobson .............. A61M 5/142 604/67 |
| 2009/0043252 A1 | 2/2009 | Haylor et al. |
| 2009/0069749 A1 | 3/2009 | Miller et al. |
| 2009/0153058 A1 | 6/2009 | Feng et al. |
| 2009/0153463 A1 | 6/2009 | Arrizza et al. |
| 2009/0153595 A1 | 6/2009 | Cozmi et al. |
| 2009/0157432 A1 | 6/2009 | Palmroos et al. |
| 2009/0171289 A1 | 7/2009 | Davis et al. |
| 2009/0177180 A1 | 7/2009 | Rubalcaba, Jr. et al. |
| 2009/0177991 A1 | 7/2009 | Davis et al. |
| 2009/0177992 A1 | 7/2009 | Rubalcaba, Jr. et al. |

(56) References Cited

U.S. PATENT DOCUMENTS

| | | |
|---|---|---|
| 2009/0183105 A1 | 7/2009 | Teel, IV et al. |
| 2009/0183147 A1 | 7/2009 | Davis et al. |
| 2009/0247982 A1 | 10/2009 | Krulevitch et al. |
| 2010/0010647 A1 | 1/2010 | Schroeder et al. |
| 2010/0100037 A1 | 4/2010 | Cozmi et al. |
| 2011/0040247 A1 | 2/2011 | Mandro et al. |
| 2011/0097229 A1 | 4/2011 | Cauley III et al. |
| 2011/0106004 A1 | 5/2011 | Eubanks et al. |
| 2011/0106318 A1 | 5/2011 | Ledford |
| 2011/0184383 A1 | 7/2011 | Hasegawa |
| 2011/0300010 A1 | 12/2011 | Jamagin et al. |
| 2011/0313358 A1 | 12/2011 | Hariharesan et al. |
| 2012/0004624 A1 | 1/2012 | Brown et al. |
| 2012/0023808 A1 | 2/2012 | Lagunas-Solar et al. |
| 2012/0083760 A1* | 4/2012 | Ledford ............... A61M 5/14 604/152 |
| 2012/0101437 A1 | 4/2012 | Gagliardoni et al. |
| 2012/0130308 A1 | 5/2012 | Silkaitis et al. |
| 2012/0130309 A1 | 5/2012 | Hariharesan et al. |
| 2012/0266964 A1 | 10/2012 | West et al. |
| 2012/0266965 A1 | 10/2012 | Hariharesan et al. |
| 2013/0053820 A1 | 2/2013 | Estes et al. |
| 2013/0115120 A1 | 5/2013 | Jamagin et al. |
| 2013/0131585 A1 | 5/2013 | Eubanks et al. |
| 2013/0267899 A1 | 10/2013 | Robert et al. |
| 2013/0272773 A1 | 10/2013 | Kamen et al. |
| 2013/0281965 A1 | 10/2013 | Kamen et al. |
| 2014/0100526 A1 | 4/2014 | Ueda et al. |
| 2014/0188076 A1 | 7/2014 | Kamen et al. |
| 2014/0200510 A1 | 7/2014 | Agard et al. |
| 2014/0249500 A1 | 9/2014 | Estes |
| 2014/0259837 A1* | 9/2014 | Belliveau ............... G16H 20/17 211/49.1 |
| 2014/0271246 A1 | 9/2014 | Zollinger et al. |
| 2014/0271247 A1 | 9/2014 | Abal |
| 2014/0276424 A1 | 9/2014 | Davis et al. |
| 2014/0317929 A1 | 10/2014 | Robert et al. |
| 2014/0358111 A1 | 12/2014 | Brewer et al. |
| 2015/0018766 A1 | 1/2015 | Nakanishi et al. |
| 2015/0023808 A1 | 1/2015 | Zhu |
| 2015/0041419 A1 | 2/2015 | Hawegawa |
| 2015/0133890 A1 | 5/2015 | Wander et al. |
| 2015/0157791 A1 | 6/2015 | Desch et al. |
| 2015/0265768 A1 | 9/2015 | Vazquez et al. |
| 2015/0273140 A1 | 10/2015 | Bresina et al. |
| 2015/0275887 A1 | 10/2015 | Koyama et al. |
| 2015/0297832 A1 | 10/2015 | Blomquist |
| 2015/0314066 A1 | 11/2015 | Shimizu |
| 2016/0058939 A1 | 3/2016 | Brewer et al. |
| 2016/0084434 A1 | 3/2016 | Janway et al. |
| 2016/0228633 A1 | 8/2016 | Welsch et al. |
| 2016/0235910 A1 | 8/2016 | Damiano et al. |
| 2016/0250410 A1 | 9/2016 | Traversaz et al. |
| 2017/0028126 A1 | 2/2017 | Moosai |
| 2017/0100536 A1 | 4/2017 | Estes |
| 2017/0182244 A1 | 6/2017 | Blomquist |
| 2017/0189605 A1 | 7/2017 | Blomquist |
| 2017/0203032 A1 | 7/2017 | Dowden et al. |
| 2017/0213012 A1 | 7/2017 | O'Scolai et al. |
| 2017/0258985 A1 | 9/2017 | Adams et al. |
| 2017/0277851 A1 | 9/2017 | Adams et al. |
| 2017/0281864 A1 | 10/2017 | Searle et al. |
| 2018/0117241 A1 | 5/2018 | Amborn et al. |
| 2018/0140770 A1 | 5/2018 | Hetchler et al. |
| 2018/0202429 A1 | 7/2018 | Bresina et al. |
| 2018/0353678 A1 | 12/2018 | Adams et al. |
| 2020/0179592 A1 | 6/2020 | Adams et al. |

FOREIGN PATENT DOCUMENTS

| | | |
|---|---|---|
| AU | 2011293619 B2 | 9/2015 |
| AU | 2010286957 B2 | 10/2015 |
| AU | 2009348755 B2 | 11/2015 |
| AU | 2010208447 B2 | 11/2015 |
| AU | 2010273694 B2 | 12/2015 |
| AU | 2011280208 B2 | 12/2015 |
| AU | 2012258687 B2 | 2/2016 |
| AU | 2013260724 B2 | 4/2016 |
| AU | 2015328081 B2 | 7/2016 |
| AU | 2015330980 B2 | 7/2016 |
| AU | 2012340056 B2 | 11/2016 |
| AU | 2014277760 B2 | 2/2017 |
| AU | 2016200525 B2 | 2/2017 |
| AU | 2012387311 B2 | 7/2017 |
| AU | 2015209670 B2 | 7/2017 |
| AU | 2014207809 B2 | 8/2017 |
| AU | 2013230954 B2 | 9/2017 |
| AU | 2015209669 B2 | 10/2017 |
| AU | 2014234996 B2 | 12/2017 |
| AU | 201810386 | 2/2018 |
| AU | 2012258687 C1 | 3/2018 |
| AU | 2013361569 B2 | 5/2018 |
| AU | 2014225658 B2 | 5/2018 |
| AU | 2018302257 A1 | 1/2020 |
| AU | 2018388965 A1 | 7/2020 |
| AU | 2019263493 A1 | 11/2020 |
| CA | 2812551 C | 6/2015 |
| CA | 2711244 C | 2/2016 |
| CA | 2751513 C | 4/2016 |
| CA | 2765880 C | 4/2016 |
| CA | 2712930 C | 7/2016 |
| CA | 2704411 C | 9/2016 |
| CA | 2765967 C | 10/2016 |
| CA | 2765968 C | 10/2016 |
| CA | 2928503 C | 10/2016 |
| CA | 2928505 C | 11/2016 |
| CA | 2709193 C | 1/2017 |
| CA | 2812555 C | 2/2017 |
| CA | 2713028 C | 4/2017 |
| CA | 2712945 C | 6/2017 |
| CA | 2749557 C | 6/2017 |
| CA | 2750335 C | 6/2017 |
| CA | 2702385 C | 7/2017 |
| CA | 2712947 C | 7/2017 |
| CA | 2720492 C | 7/2017 |
| CA | 2866022 C | 8/2017 |
| CA | 2712950 C | 10/2017 |
| CA | 2560996 C | 11/2017 |
| CA | 2772599 C | 11/2017 |
| CA | 2805738 C | 11/2017 |
| CA | 3027961 A1 | 12/2017 |
| CA | 2768205 C | 1/2018 |
| CA | 2780286 C | 1/2018 |
| CA | 2767986 C | 4/2018 |
| CA | 3069538 A1 | 1/2019 |
| CA | 3086175 A1 | 6/2019 |
| CA | 179406 | 9/2019 |
| CA | 3099115 A1 | 11/2019 |
| CN | 101990446 A | 3/2011 |
| CN | 102065931 A | 5/2011 |
| CN | 102292117 A | 12/2011 |
| CN | 102481447 A | 5/2012 |
| CN | 104334209 A | 2/2015 |
| CN | 104640584 A | 5/2015 |
| CN | 201730157329.3 | 7/2018 |
| CN | 201830031970.7 | 11/2018 |
| CN | 109414545 A | 3/2019 |
| CN | 110944697 A | 3/2020 |
| CN | 111683701 A | 9/2020 |
| CN | 112074313 A | 12/2020 |
| DE | 4030368 C1 * | 11/1991 |
| DE | 10348653 A1 | 5/2005 |
| EM | 003933993-0001 | 5/2017 |
| EM | 003933993-0002 | 5/2017 |
| EM | 003933993-0003 | 5/2017 |
| EM | 003933993-0004 | 5/2017 |
| EM | 003933993-0005 | 5/2017 |
| EM | 003934447-0001 | 5/2017 |
| EM | 003934447-0002 | 5/2017 |
| EM | 003934447-0003 | 5/2017 |
| EM | 003934447-0004 | 5/2017 |
| EM | 4680353-0001 | 1/2018 |
| EM | 4680353-0002 | 1/2018 |

(56) References Cited

FOREIGN PATENT DOCUMENTS

| | | |
|---|---|---|
| EM | 4680353-0003 | 1/2018 |
| EP | 0477551 A1 | 4/1992 |
| EP | 0780134 A1 | 6/1997 |
| EP | 0655107 B1 | 10/2002 |
| EP | 0999860 B1 | 1/2004 |
| EP | 0839062 B1 | 9/2004 |
| EP | 1186311 B1 | 11/2004 |
| EP | 1616588 B1 | 3/2006 |
| EP | 1664536 B1 | 10/2007 |
| EP | 1787024 B1 | 11/2009 |
| EP | 1768723 B1 | 8/2010 |
| EP | 2077874 B1 | 9/2011 |
| EP | 1557187 B1 | 4/2012 |
| EP | 2445573 B1 | 1/2014 |
| EP | 2542781 B1 | 3/2014 |
| EP | 2398533 B1 | 4/2014 |
| EP | 2298388 B1 | 7/2015 |
| EP | 2298389 B1 | 8/2015 |
| EP | 2924289 A1 | 9/2015 |
| EP | 2596819 B1 | 11/2015 |
| EP | 2319551 B1 | 1/2016 |
| EP | 1381889 B1 | 3/2016 |
| EP | 2254615 B1 | 3/2016 |
| EP | 2298378 B1 | 3/2016 |
| EP | 2252346 B1 | 4/2016 |
| EP | 2519288 B1 | 4/2016 |
| EP | 2173433 B1 | 5/2016 |
| EP | 2736551 B1 | 5/2016 |
| EP | 2252347 B1 | 7/2016 |
| EP | 2254616 B1 | 7/2016 |
| EP | 2570826 B1 | 8/2016 |
| EP | 2173402 B1 | 9/2016 |
| EP | 2252345 B1 | 9/2016 |
| EP | 2453950 B1 | 10/2016 |
| EP | 2621452 B1 | 11/2016 |
| EP | 2606922 B1 | 2/2017 |
| EP | 2197513 B1 | 4/2017 |
| EP | 2295091 B1 | 4/2017 |
| EP | 2604301 B1 | 5/2017 |
| EP | 2883559 B1 | 6/2017 |
| EP | 2902048 B1 | 6/2017 |
| EP | 2381978 B1 | 7/2017 |
| EP | 2896417 B1 | 7/2017 |
| EP | 1680176 B1 | 8/2017 |
| EP | 2736564 B1 | 8/2017 |
| EP | 1881786 B1 | 11/2017 |
| EP | 2183016 B1 | 11/2017 |
| EP | 3037117 B1 | 12/2017 |
| EP | 2700424 B1 | 1/2018 |
| EP | 2260891 B1 | 3/2018 |
| EP | 2968741 B1 | 5/2018 |
| EP | 3085402 B1 | 5/2018 |
| EP | 3471796 A1 | 4/2019 |
| EP | 3655065 A2 | 5/2020 |
| EP | 3727497 A1 | 10/2020 |
| GB | 2302140 B | 4/1998 |
| GB | 2338992 B | 9/2000 |
| IL | 61475 | 1/2018 |
| IL | 60330 | 4/2018 |
| IL | 61476 | 4/2018 |
| IL | 61546 | 11/2018 |
| JP | 3267404 B2 | 3/2002 |
| JP | 3290263 B2 | 6/2002 |
| JP | 3382622 B2 | 3/2003 |
| JP | 3885018 B2 | 2/2007 |
| JP | 3931013 B2 | 6/2007 |
| JP | 4394072 B2 | 1/2010 |
| JP | 4507233 B2 | 7/2010 |
| JP | 4674689 B2 | 4/2011 |
| JP | 4805724 B2 | 11/2011 |
| JP | 4833732 B2 | 12/2011 |
| JP | 4939707 B2 | 5/2012 |
| JP | 2012107555 A | 6/2012 |
| JP | 2012516208 A | 7/2012 |
| JP | 5180479 B2 | 4/2013 |
| JP | 5235042 B1 | 7/2013 |
| JP | 2013153864 A | 8/2013 |
| JP | 5308575 B2 | 10/2013 |
| JP | 5457365 B2 | 4/2014 |
| JP | 5543493 B2 | 7/2014 |
| JP | 5595930 B2 | 9/2014 |
| JP | 5619029 B2 | 11/2014 |
| JP | 5720193 B2 | 5/2015 |
| JP | 2015181554 A | 10/2015 |
| JP | 2016508045 A | 3/2016 |
| JP | 3378054 B2 | 2/2017 |
| JP | 1588670 | 9/2017 |
| JP | 1588671 | 9/2017 |
| JP | 1591102 | 10/2017 |
| JP | 1619335 | 11/2018 |
| JP | 2019525784 A | 9/2019 |
| JP | 2020527417 A | 9/2020 |
| NZ | 423975 | 4/2018 |
| WO | WO 2001/036027 A1 | 5/2001 |
| WO | WO 2004/037322 A1 | 5/2004 |
| WO | WO 2005/037349 A2 | 4/2005 |
| WO | WO 2010/023915 A1 | 3/2010 |
| WO | WO 2010/088143 A1 | 8/2010 |
| WO | WO 2010/088144 A1 | 8/2010 |
| WO | WO 2010/149187 A1 | 12/2010 |
| WO | WO 2011/008619 A1 | 1/2011 |
| WO | WO 2011/008621 A1 | 1/2011 |
| WO | WO 2011/008624 A2 | 1/2011 |
| WO | WO 2011/025588 A1 | 3/2011 |
| WO | WO 2011/025589 A1 | 3/2011 |
| WO | WO 2012/009697 A1 | 1/2012 |
| WO | WO 2012/039300 A1 | 3/2012 |
| WO | WO 2014/089008 A2 | 6/2014 |
| WO | WO 2014/100744 A2 | 6/2014 |
| WO | WO 2014/159466 A1 | 10/2014 |
| WO | WO 2016/014335 A1 | 1/2016 |
| WO | WO 2016/018552 A1 | 2/2016 |
| WO | WO 2016/179389 A1 | 11/2016 |
| WO | WO 2016/183342 A1 | 11/2016 |
| WO | WO 2016/196098 A1 | 12/2016 |
| WO | WO 2017/218927 A1 | 12/2017 |
| WO | WO 2018/022355 A1 | 2/2018 |
| WO | WO 2019/018658 A2 | 1/2019 |
| WO | WO 2019/055516 A2 | 3/2019 |
| WO | WO 2019/125941 A1 | 6/2019 |
| WO | WO 2019/213496 A1 | 11/2019 |

OTHER PUBLICATIONS

US 9,320,848 B2, 04/2016, Grant et al. (withdrawn)
US 9,867,954 B2, 01/2018, Grant et al. (withdrawn)
DE 4030368C1 translation (Year: 1991).*
memteknoloji.com, Stackable Syringe Pump Dixson Instilar 1438, undated online product page, retrieved Sep. 18, 2018 from <URL:http://memteknoloji.com/dixion/www.dixion.de/en/catalogue/intensivstation-4/injektionspumpen-4/stapelbare-injektionspumpe-instilar-1438-3.h-tml> (Year: 2018).
Emsworld.com, Space Infusion Pump System, undated online product page, retrieved Sep. 18, 2018 from <URL:https://www.emsworld.com/product/10264356/space-infusion-pump-sys-tem> (Year: 2018).
FMH Employees, "Pediatric Pump Operation: Medfusion Syringe Pump," Mar. 28, 2012, Retrieved from the Internet (Jun. 27, 2019).
PCT Application No. PCT/US2018/042907, Search Report and Written Opinion dated Jan. 15, 2020, 15 pages.
Application and File History for U.S. Appl. No. 15/733,222, filed Jun. 11, 2020. Inventors: Adams et al.
Application and File History for U.S. Appl. No. 16/309,909, filed Dec. 13, 2018. Inventors: Adams et al.
Application and File History for U.S. Appl. No. 17/250,010, filed Oct. 30, 2020. Inventors: Peterson et al.
Application and File History for U.S. Appl. No. 29/583,354, filed Nov. 4, 2016. Inventors: Lacy et al.
Application and File History for U.S. Appl. No. 29/583,359, filed Sep. 11, 2018. Inventors: Lacy et al.
Application and File History for U.S. Appl. No. 29/583,361, filed Feb. 20, 2018. Inventors: Lacy et al.

(56) References Cited

OTHER PUBLICATIONS

Application and File History for U.S. Appl. No. 29/586,520, filed Jul. 17, 2018, Inventors: Lacy et al.

* cited by examiner

HOUSING ARRANGEMENTS FOR INFUSION PUMPS

CROSS-REFERENCE TO RELATED APPLICATIONS

The present application claims priority to U.S. Provisional Patent Application No. 62/534,407, filed on Jul. 19, 2017, which is hereby fully incorporated herein by reference.

TECHNICAL FIELD

Embodiments relate generally to medical devices and, more particularly, to housing arrangements for infusion pumps in the form of syringe pumps and large volume pumps (LVPs).

BACKGROUND

In the medical arts, infusion pumps have been useful for managing the delivery and dispensation of a prescribed amount or dose of a drug, fluid, fluid-like substance, or medicament (hereinafter, collectively, an "infusate") to patients. Infusion pumps can provide some significant advantages over manual infusion techniques, by accurately delivering and dispensing infusates over an extended period of time.

Infusion pumps are particularly useful for treating diseases and disorders that require regular pharmacological intervention, including cancer, diabetes, and vascular, neurological, and metabolic disorders. They also enhance the ability of healthcare providers to deliver anesthesia and manage pain. Infusion pumps are used in various settings, including hospitals, nursing homes, and other short-term and long-term medical facilities, as well as in residential care settings. Infusion pumps can include various constructions, modes of operation, and types.

Generally, infusion pumps can include a variety of types of pumps. In some cases, these infusion pumps include syringe pumps and LVPs. Depending upon their specific designs and intended uses, infusion pumps can be used to administer infusates through various delivery methods and routes, including intravenously, intraperitoneally, enterally, intra-arterially, subcutaneously, neuraxially, and specifically into an intraoperative site, epidural space, and subarachnoid space.

While various syringe pumps and LVPs have been used in medical environments for many years, these devices remain rather complex medical devices with some limitations to their efficient, effective, and safe use. Therefore, there is a need for syringe pumps and LVPs which provide greater flexibility and ease of use to operators. Moreover, due to the vital role of infusion pumps in many medical procedures and treatments, syringe pumps and LVPs which provide enhanced safety to patients are needed as well.

SUMMARY

Embodiments described or otherwise contemplated herein substantially provide the advantages of improving flexibility, ease of use, operation, as well as patient safety, among other advantages.

An embodiment relates to an infusion pump, including a housing, a user interface, a motor and a set of drive components, and a controller. The housing enables selective stacked attachment with other infusion pumps. The housing includes a top portion with a handle integrated into an outer surface that partially defines a generally U-shaped retaining feature. The housing also includes a bottom portion with a generally U-shaped projection contoured to selectively mate with a retaining feature of another infusion pump. The user interface provides a front side to the housing that receives commands regarding infusion pump operation. The motor and set of drive components are at least partially located within the housing and mechanically direct infusion of an infusate. The controller is located within the housing and controls operation of the motor and the set of drive components.

An embodiment relates to a syringe pump, including a syringe receptacle, a syringe plunger driver assembly, and a housing. The syringe receptacle is configured to receive a syringe of an infusate. The syringe plunger driver assembly is located adjacent the syringe receptacle and directs the infusate from the syringe to a patient based on movement and force against a plunger of the syringe. The housing is coupled with the syringe receptacle and has a front side that includes a graphical user interface (GUI) display for controlling the syringe pump. The syringe receptacle is located on the front side of the housing vertically adjacent the GUI display in non-overlapping and non-visually obscuring alignment. The housing is configured such that both the syringe in the syringe receptacle and the entire GUI display are substantially visible on the front side of the housing.

An embodiment includes an infusion pump assembly. The infusion pump assembly includes a first infusion pump having a housing and a user interface with a display screen. The infusion pump assembly also has a "headless" infusion pump having no display screen. The headless infusion pump is releasably coupled to the housing of the first infusion pump by tongue-and-groove attachment.

An embodiment relates to a "field replaceable unit" for infusion pumps. The field replaceable unit includes a rear housing for an infusion pump. The rear housing includes a top portion and a bottom portion. The top portion has an integrally formed handle structure and a set of grooves. The bottom portion has a projection for releasable coupling with grooves in another rear housing. The rear housing includes a power receptacle and an Ethernet port. The rear housing interchangeably couples with a set of medication delivery components, a control system, and a display of either a LVP or a syringe pump.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
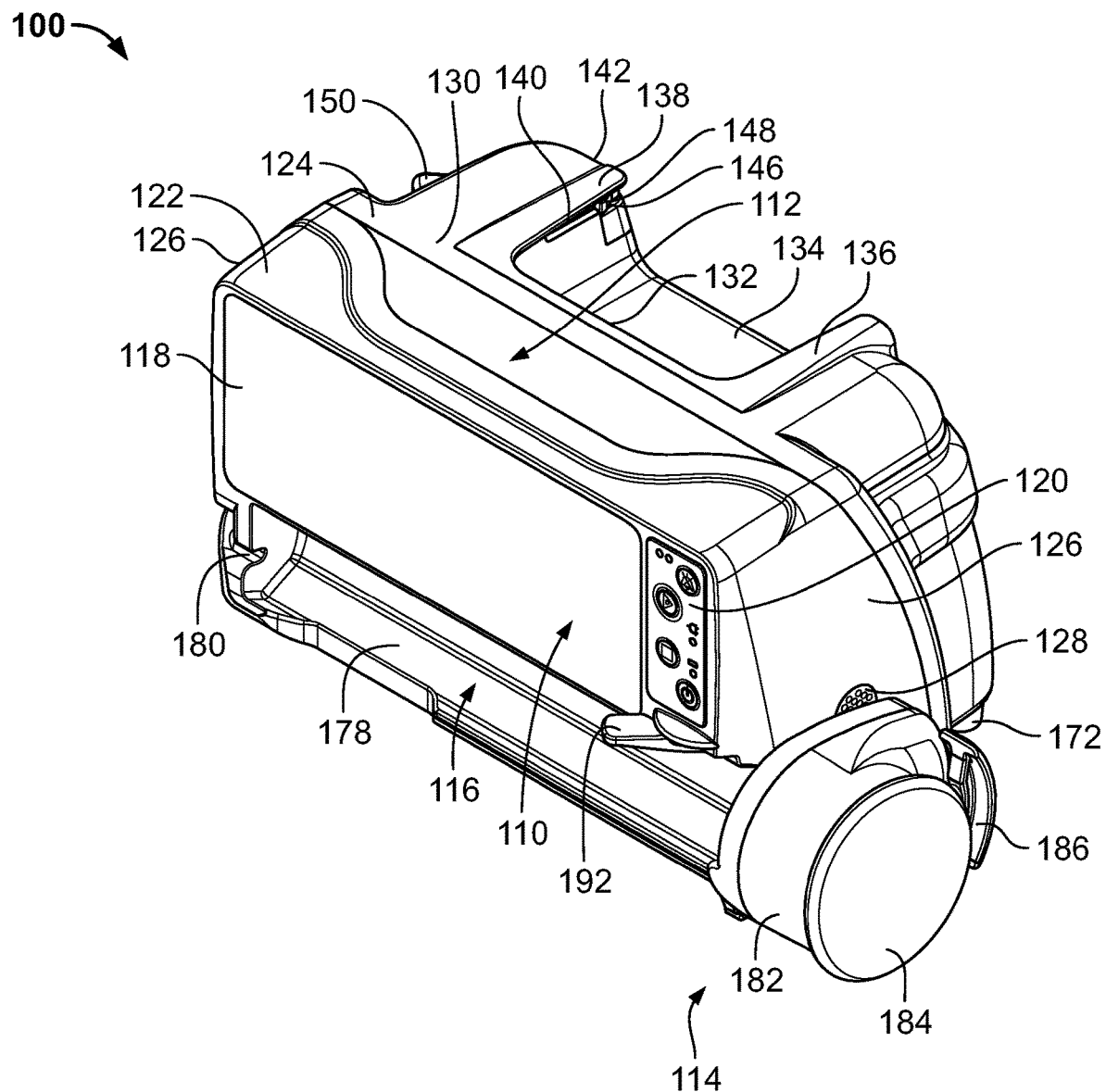
FIG. 1 is front perspective view of a syringe pump, according to an embodiment.

While various embodiments are amenable to various modifications and alternative forms, specifics thereof have been shown by way of example in the drawings and will be described in detail. It should be understood, however, that the intention is not to limit the claimed subject matter to particular embodiments described. On the contrary, the intention is to cover all modifications, equivalents, and alternatives falling within the spirit and scope of the subject matter as defined by the claims.

DETAILED DESCRIPTION OF THE DRAWINGS

In FIGS. 1-7, various views of an infusion pump in the form of a syringe pump 100 are shown. Similarly, in FIGS. 8-14 various views of an infusion pump in the form of a LVP 200 are shown. Both syringe pump 100 and LVP 200 make use of field replaceable unit (FRU) designs including a plurality of individual FRUs that enable pump components to be readily upgraded or replaced. Some FRUs are common to both syringe pump 100 and LVP 200. "Syringe pumps" generally include pumps for acting on a pre-filled infusate syringe that is mechanically driven under microprocessor control to deliver a prescribed amount or dose of the infusate at a controlled rate to a patient through an infusion line fluidly connected to the syringe. Syringe pumps typically include a motor that rotates a leadscrew or adjustment mechanism, for example. The leadscrew or adjustment mechanism, in turn, activates a syringe plunger driver of the syringe pump which in turn pushes forwardly against a plunger within a barrel of the syringe. Pushing the plunger forward then forces a dose of the infusate outwardly from the syringe, into the infusion line, and to the patient as aforedescribed. As used throughout this disclosure, the term "syringe pump" is intended to generally pertain to any medical infusion pump or device which acts on a syringe to controllably force fluid outwardly therefrom.

"LVPs" can take on various forms, but are typically infusion pumps coupled to one or more reservoirs configured to hold or store a relatively large amount of infusate or infusates, such as a cassette, IV bag, or other self-contained source. As used throughout this disclosure, the term "LVP" is intended to generally pertain to any medical infusion pump or device capable of large volume infusion to a patient.

Syringe Pump

Referring first to FIGS. 1-6, syringe pump 100 generally includes a user interface 110, housing 112, syringe plunger driver assembly 114, and syringe receptacle 116. Various other features of the syringe pump 100, including some that are internal or partially or fully obscured by the housing 112, will be later described with reference to the system diagram of FIG. 7.

As seen in FIG. 1, user interface 110 generally includes a display screen 118 and a keypad 120. Display screen 118 can be a rectangular, color LCD screen, and can be a touchscreen in certain embodiments. Display screen 118 can be any type of GUI display for use in controlling the syringe pump 100. In some embodiments, the display screen 118 can be configured to permit display of four lines of text, up to thirty characters long each. Accordingly, this size of display screen 118 advantageously enables viewing information such as, for example, drug names of significant length.

In some embodiments, certain commands or instructions are not controlled by a touchscreen, such as a display screen 118 and, instead, are controlled by a keypad 120. Keypad 120 is located adjacent to the display screen 118 and presents a variety of buttons and indicator lights. In some embodiments, push buttons requiring physical mechanical actuation are used on the keypad 120 for certain user commands, including: on/off power; audible alarm mute; start infusion, and stop infusion. Additional or fewer buttons on keypad 120 are contemplated as well. Physical mechanical actuation buttons, for primary or redundant purposes, provide increased safety and reliability to operators in cases where the touchscreen of a display 118 does not function properly, or is otherwise difficult to manipulate correctly. Having a user interface 110 including both a display screen 118 and a keypad 120, accordingly, provides the flexibility of a screen interface as well as the enhanced safety and reliability of physical control buttons.

The housing 112 generally forms a protective shell surrounding the internal components of the syringe pump 100. In some embodiments, the user interface 110 may be considered part of the housing 112. The housing 112 can be characterized as generally comprising a front housing assembly 122 and a rear housing assembly 124. Front housing assembly 122 generally surrounds the LCD display screen 118, keypad 120 and other components around the user interface 110. The front housing assembly 122 includes side panels 126 along the front portion of the syringe pump 100. A grouping of small holes can be located on one or both side panels 126 of the front housing 122 for audio speakers 128.

Figure 4:
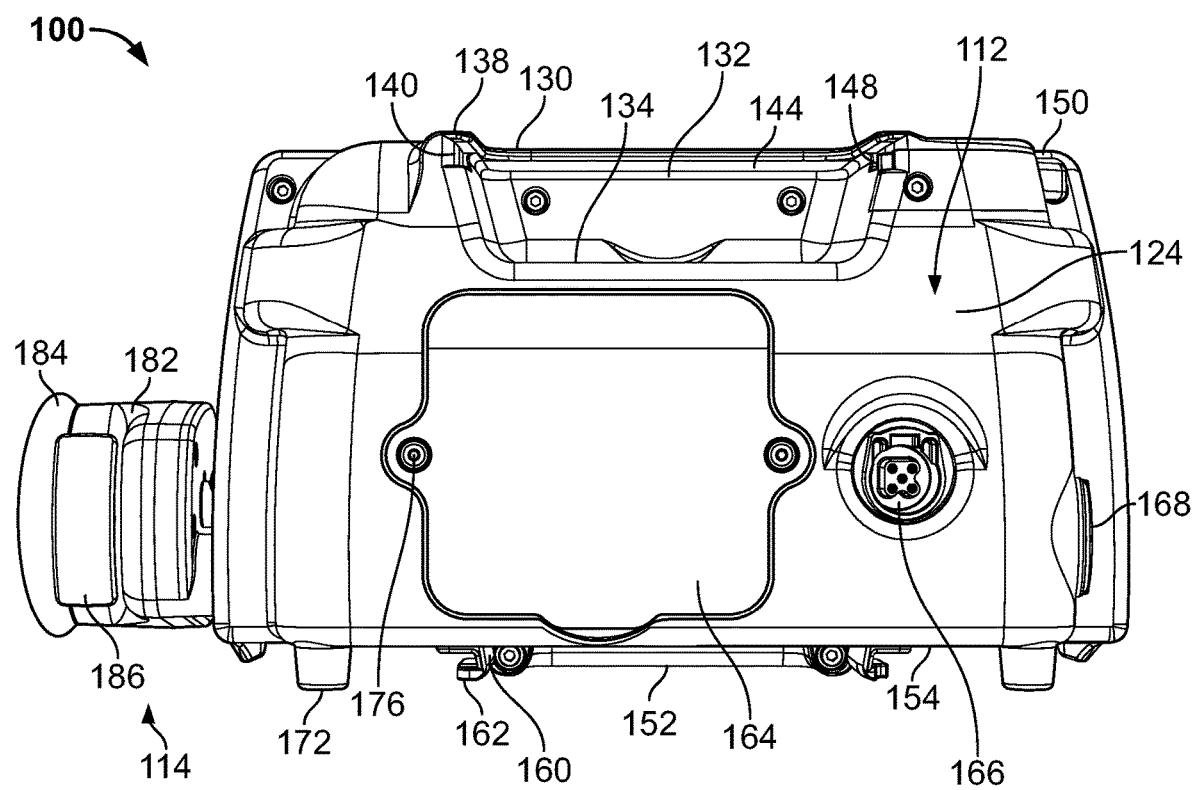
FIG. 4 is a rear view of a syringe pump, accordingly to an embodiment.

As illustrated in, for example, FIG. 4, rear housing assembly 124 generally includes a variety of contoured surfaces and shapes to protect the internal components of the syringe pump 100. The top portion 130 of the rear housing assembly 124 provides features defining a handle 132. The handle 132 is integrally formed into the outer surface of the rear housing assembly 124 and is partially defined by a central recess 134 in the top portion 130 of housing 112. The handle 132 provides a convenient structure for grasping, manipulating, and moving the syringe pump 100. The integrally formed nature of the handle 132 with the rest of the housing 112 provides advantages in medical settings due to an ability to be rather easily cleaned. In contrast, a non-integral handle and housing arrangement having a separate hinge or attachment features, could present a much more difficult component or assembly to clean.

Figure 5:
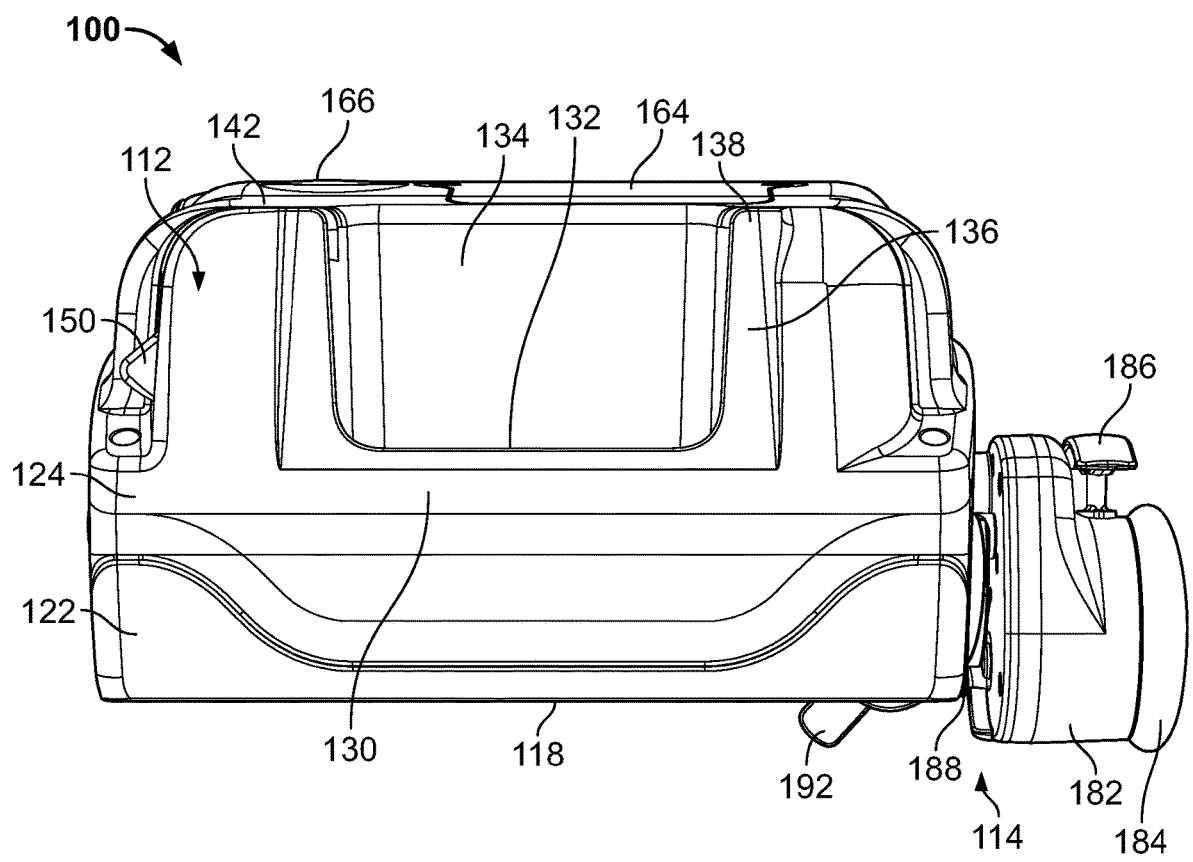
FIG. 5 is a top view of a syringe pump, according to an embodiment.
Figure 6:
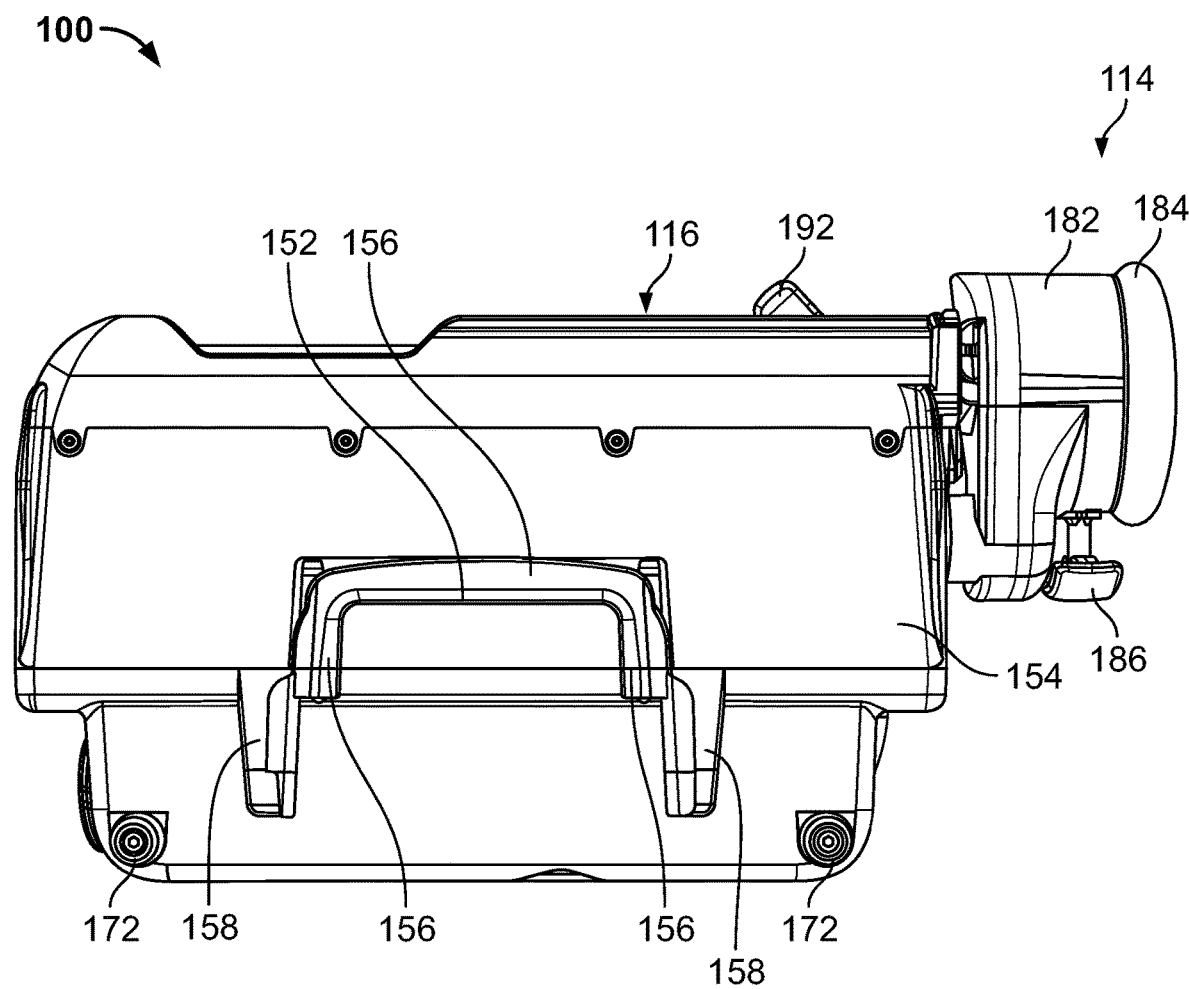
FIG. 6 is a bottom view of a syringe pump, according to an embodiment.

As illustrated in, for example, FIG. 5, handle 132 is further part of a generally U-shaped retaining feature 136. Generally U-shaped retaining feature 136 can provide releasable interlocking engagement with other infusion pumps or related components. As illustrated in the perspective views of FIGS. 1 and 2, and particularly the top view of FIG. 5, the generally U-shaped retaining feature 136 can be seen. Generally U-shaped retaining feature 136 includes an upper lip portion 138 that extends inwardly around the central recess 134 located at the top portion 130 of the housing 112. The upper lip portion 138 extends around three sides of the recess 134, to form a general "U" shape when viewed from above. The section of the upper lip portion 138 in the middle of the general "U" shape partially comprises the handle 132. Beneath an overhang of this section of the upper lip portion 138 is a more deeply recessed space in which a user attempting to lift the syringe pump 100 can place his or her fingers and readily grasp the handle 132 from above.

In addition to the upper lip portion 138, the generally U-shaped retaining feature 136 further includes a set of receiving grooves 140 (as partially illustrated in, for example, FIGS. 2 and 4) underneath the upper lip portion 138, adjacent the rear face 142 of the rear housing assembly 124 at each end of the "U" shape. The receiving grooves 140 are slots which progressively narrow in structure and converge inwardly from the rear face 142 of the rear housing assembly 124. Forward of the receiving grooves 140 is a narrowed section 144 of housing, against which an inserted member can abut.

As illustrated in, for example, FIGS. 1 and 4, a latch 146 having a catch 148 is located on one side of the set of receiving grooves 140. This catch 148 is spring-loaded and able to click into place to hold a member loaded in the receiving grooves 140. Opposite these latch 146 and catch 148 members, on the side of the upper portion of the housing 112, is a further pump latch button 150. Pump latch button 150 can be pressed to unlock the latch 146 and catch 148 members such that a pump or component that is stacked and engaged to the handle 132 by receiving grooves 140, can be released and removed.

Figure 2:
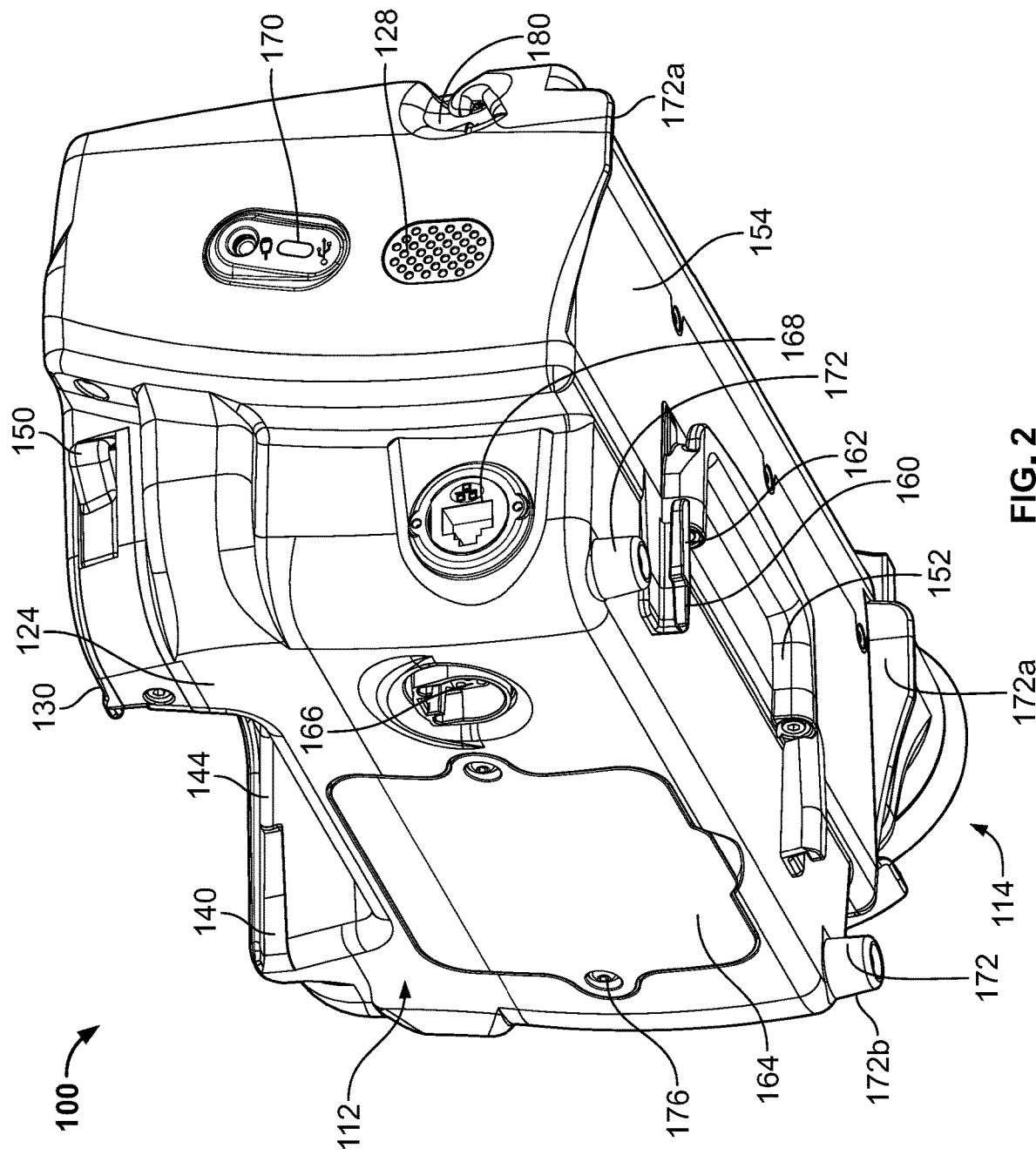
FIG. 2 is a rear perspective view of a syringe pump, according to an embodiment.

As shown in FIG. 2, rear housing assembly 124 also includes a downwardly extending and generally U-shaped projection 152 on a bottom portion 154 of pump 100. The generally U-shaped projection 152 is a protruding structure that can be placed in grooves (similar to receiving grooves 140 from other similar or identical pumps or devices). The generally U-shaped projection 152 is located on the bottom portion 154 of the rear housing assembly 124. As most clearly seen in the bottom view of the syringe pump 100 in FIG. 6, the generally U-shaped projection 152 includes a forward portion 156 and rearward portions 158.

The forward portion 156 of the generally U-shaped projection 152 is located in the middle of the "U" shape. The forward portion 156 forms a tightly curved "U" shape. The forward portion 156 provides a surface that can abut up against and mate with a corresponding surface of a pump or device, similar to that of narrowed section 144 of the generally U-shaped retaining feature 136 on the top portion 130 of the housing 112. The rearward portions 158 of the generally U-shaped projection 152 each provide segments of wider separation than the sides of the forward portion 156. The rearward portions 158 of the generally U-shaped projection 152 include a flange 160 with an outwardly extending lip 162 as illustrated in, for example, FIGS. 2 and 4. When taken together, the flange 160 and outwardly extending lip 162 provide a feature for sliding engagement. The generally U-shaped projection 152, accordingly, provides a structure that can be releaseably slid into and engaged below an upper lip portion 138 and within receiving grooves 140 of the generally U-shaped retaining feature 136. This type of coupling effectively provides so-called "tongue and groove" retention. Accordingly, the generally U-shaped retaining feature 136 and generally U-shaped projection 152 can enable multiple infusion pumps 100 to be stacked vertically on top of one another in an engaged tongue and groove arrangement when the pumps include those features compatibly.

In FIG. 2, other features that can be seen on the back, sides, and bottom of the housing 112 include: a battery door cover 164, power receptacle 166, Ethernet connector 168, USB port 170, and support structures or "mounting feet" 172 (that will be described in further detail). In general, battery door cover 164 provides a plate that can be removed to access a battery 174 (as depicted schematically in FIG. 7) located within the housing 112 of syringe pump 100. Battery door cover 164 is generally rectangular in shape but includes curved perimeter features to accommodate removable fasteners 176. Due to its ease of access and removal, battery 174 can be characterized as being a separate FRU for purposes of removal and replacement.

With reference again to, for example, FIGS. 2 and 4, power receptacle 166 is located in the back of the rear housing assembly 124 of the syringe pump 100. Power receptacle 166 may interface directly with a power cord, or alternatively, with a power connector contained on a pump rack. In the case of connection to a power cord, the power receptacle 166 provides a mechanical lock and retaining feature that prevents the power cord from being unintentionally pulled from operative engagement with the syringe pump 100. This can be useful to prevent power loss in an event of a slightly or unintentionally pulled or bumped power cord. The power receptacle 166 also has a tapered bevel structure which helps to accommodate interfacing with a power connector on a rack where the user typically has limited visibility for ensuring alignment.

Male and female connector portions can be keyed or otherwise restricted or controlled in orientation such that interlocking of the male and female components can only be made in a specified orientation. This can be advantageous in assisting proper alignment of pins, e.g., (+) to (+), and (−) to (−). The power cord connector can be keyed such that it cannot be connected in an improper orientation. In particular, the power cord connector can be a "right angle" connector, in some embodiments, yielding a low profile to decrease possible entanglements.

An Ethernet connector 168 is located on the side of housing 112 (in this example, near a back lower portion of the syringe pump 100). This location provides convenient access to other pumps, racks or communication devices that utilize Ethernet for data transfer. Ethernet connector 168 can be "ingress-protection" (or "IPX") rated and does not require a cover. Similarly, USB port 170 is located on a side of housing 112 (in this example, near speaker 128). USB port 170 can have a cover and can be a so-called "on-the-go" connector for use with a variety of peripheral devices and applications.

Also designed to provide the stackable and user friendly design of syringe pump 100 are a set of support structures or mounting feet 172. In this example of pump 100, mounting feet 172 include two front mounting feet 172a and two rear mounting feet 172b. Front mounting feet 172a are extensions of the sides of housing 112 and rear mounting feet 172b are components that act to raise a back side of the housing 112. Rear mounting feet 172b provide clearance to the bottom portion 154 of the housing 112, such that the generally U-shaped projection 152 can extend downwardly without interfering with or causing disruption to physical stability of the pump 100. Similarly, in general, the mounting feet 172 are positioned so that stacked infusion pumps will not interfere with one another.

Also shown in FIGS. 1-6, is a syringe receptacle 116 and syringe plunger driver assembly 114. Syringe receptacle 116 includes an elongate cavity extending across the front of the syringe pump 100. Syringe receptacle 116 is located directly below the display screen 118 of the user interface 110. Location of the syringe receptacle 116 below the user interface 110 is advantageous in a number of respects. A syringe receptacle location below the user interface 110 aids in preventing leakages, fluid drips, or other unwanted contaminants from interfering with the display 118, keypad 120 or other potentially damageable electronic and mechanical features. In this location, the syringe receptacle 116 is somewhat spatially isolated from the remainder of the syringe pump 100 in the event of damages from syringe loading, unloading, or manipulation.

Syringe receptacle 116 contains a syringe ledge 178 on which a syringe can be operatively positioned. Syringe receptacle 116 effectively provides a cavity in the syringe pump 100 that remains open to the front of the pump 100 such that a loaded syringe is readily and substantially visible. Since the display screen 118 is located above the syringe receptacle 116, the screen 118 is generally not visually obstructed by presence of a syringe in pump 100. This non-overlapping and non-visually obscuring alignment of the receptacle and the screen simultaneously provides good visibility of both the syringe and display screen 118 in operation of pump 100.

Syringe receptacle 116 further includes an infusion line retention passage 180 (or tube guide) at one end, located opposite the end adjacent the syringe plunger driver assembly 114. The retention passage 180 provides a narrow segment in which an infusion line can pass. Specifically, retention passage 180 provides structural features which an infusion line can be looped against or around. The retention passage 180, accordingly, provides resistance from an infusion line being unintentionally pulled away from the syringe pump 100. Such pulling of the infusion line will meet resistance from the retention passage 180, rather than at the point where the infusion line is connected to a syringe located within the syringe receptacle 116.

Figure 3:
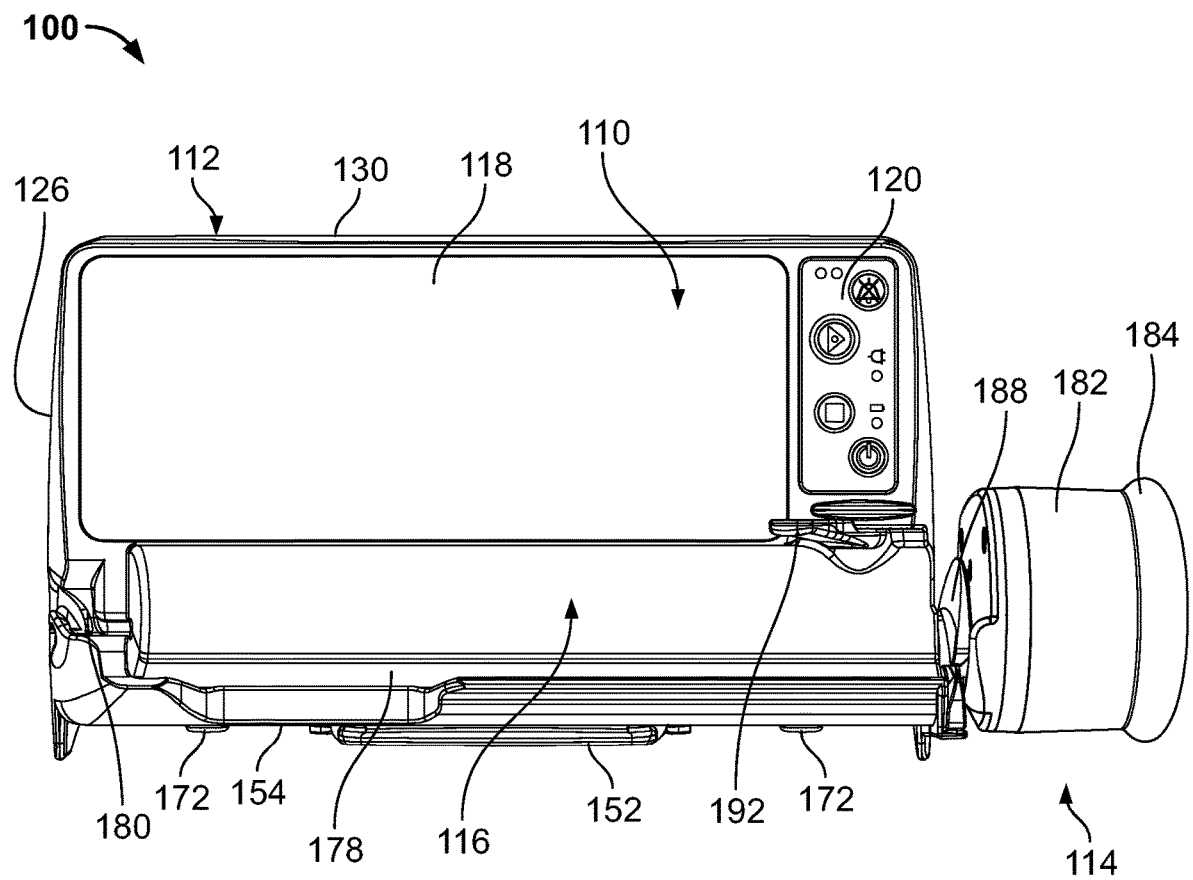
FIG. 3 is a front view of a syringe pump, according to an embodiment.

As illustrated in, for example, FIGS. 1 and 3, syringe plunger driver assembly 114 is substantially located at an end of the syringe receptacle 116. Plunger driver assembly 114 includes a plunger driver 182, bumper 184, trigger 186, and flipper 188, among other components. The plunger driver assembly 114 is responsible for controlling delivery of a prescribed amount or dose of an infusate from a syringe in the pump 100 to a patient by mechanically depressing a plunger in the syringe to deliver the infusate at a controlled rate through an infusion line fluidly connected to the syringe. More specifically, a motor 190 rotates a leadscrew which, in turn, causes the plunger driver 182 that is operatively coupled to the leadscrew to move in a direction of the syringe receptacle 116. This movement then pushes the plunger within a barrel of the syringe located within the receptacle 116. Pushing the syringe plunger forward acts to force a dose of infusate in the syringe outwardly from the syringe, into an infusion line, and ultimately to a patient.

In the illustrated example of pump 100, bumper 184 of the plunger driver assembly 114 can be a generally rounded, end portion of plunger driver assembly 114 opposite the syringe receptacle 116. The bumper 184 is generally larger in diameter than the central portion of the plunger driver 182 and is made of a durable material that is relatively easy and ergonomic to grip. The bumper 184 is made for aiding in one-handed manipulation of the plunger driver assembly 114. Additionally, the "padded" construction of the bumper 184 provides some resistance to unintended impacts. Accordingly, based on its size and material, the plunger driver 182 is designed to help absorb any unintentional impacts on the plunger driver assembly 114, in an event of, for example, a dropped or mishandled syringe pump 100.

The trigger 186 is positioned at the back side of the plunger driver assembly 114. Trigger 186 is spring-loaded and acts to unlock the plunger driver assembly 114 from a locked state, such that the plunger driver assembly 114 can then relatively freely slide laterally when the trigger 186 is depressed. As depicted in, for example, FIG. 3, flipper 188 is located between the syringe receptacle 116 and the main plunger driver section 182 of the plunger driver assembly 114. The flipper 188 is generally a curved arm which extends over a distal thumb-press portion of a plunger in a syringe to help to removably secure the syringe in pump 100. Also in the proximity of the plunger driver assembly 114 is a barrel clamp lever 192 located under the keypad 120 of the user interface 110. Barrel clamp lever 192 may be manipulated to further engage or disengage retaining members from around the barrel of a syringe being removably secured in pump 100.

In general, the bumper 184, trigger 186, flipper 188, and barrel clamp lever 192 are used in loading and unloading operations of syringes into or out of the syringe receptacle 116. In the case of loading operations of syringes into the syringe pump 100, an initial step is to extend the plunger driver assembly 114 outwardly, away from the syringe receptacle 116. In order to accomplish this, a user can manipulate and engage the bumper 184 on the end of the plunger driver assembly 114 using the palm of his/her hand and depress the trigger 186 on the rear side of the plunger driver assembly 114 with his/her fingers of that same hand. Depressing the trigger 188 releases the plunger driver 182 from its locked position and allows the plunger driver 182 to slide outwardly and away from receptacle 116. Accordingly, the plunger driver 182 is initially slid to a desired distance appropriate for the syringe barrel of the syringe. Next, the syringe is placed into the syringe receptacle 116 such that the end of the syringe barrel abuts the interior surface of the plunger driver assembly 114 location, opposite the bumper 184. An infusion line connected to the syringe is threaded through the retention passage 180 at the end of the syringe receptacle 116 located opposite the plunger driver assembly 114. The flipper 188 rotates to descend over the thumb-press of the plunger in the syringe barrel and the barrel clamp lever 192 is manipulated so that the syringe barrel is further held in place. The user can then manipulate the user interface 110 to control the syringe pump 100 in the desired manner.

Figure 7:
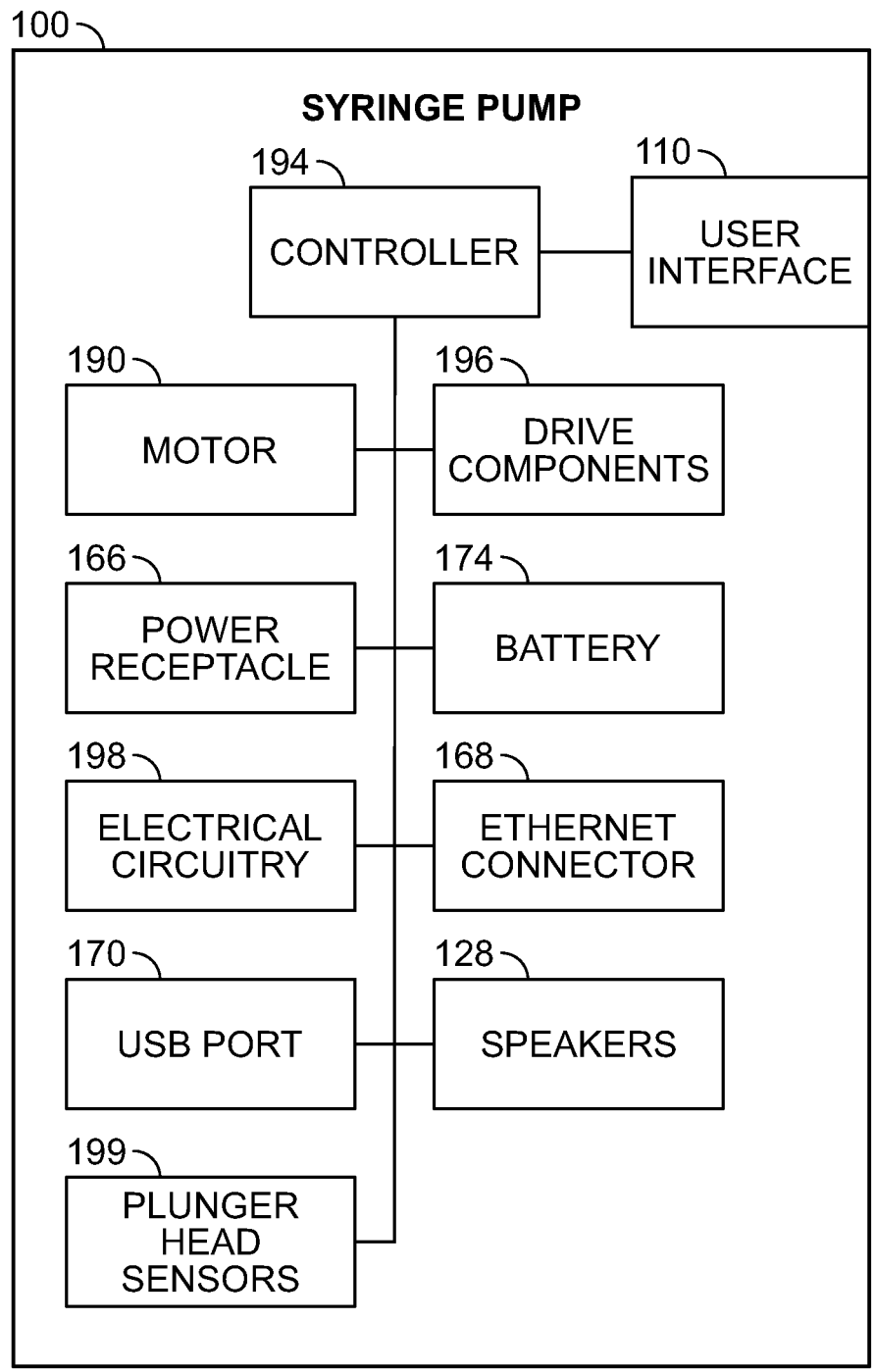
FIG. 7 is a general system diagram of a syringe pump, according to an embodiment.

FIG. 7 depicts an example of a general system diagram of the syringe pump 100, including some components that are partially or fully obscured by the housing 112. Referring also to FIGS. 1-6, the system diagram of FIG. 7 shows a diagram of a syringe pump 100, including user interface 110, controller 194, motor 190, drive components (drivetrain) 196, power receptacle 166, battery 174, electrical circuitry 198, Ethernet connector 168, USB input port 170, speakers 128, and plunger driver head sensors 199.

As discussed above, the user interface 110 serves as a source of data input for the syringe pump 110 from, for example, a medical practitioner or pump programmer. Although not specifically illustrated in FIG. 7, it is to be appreciated and understood that user interface 110 may include a touchscreen display 118, keypad 120 or a combination of these or other user interface technologies.

In this example, controller 194 is connected to the user interface and is responsible for ensuring that the pump 100 is controlled in the desired manner. Controller 194 is located in the housing 212 and controls operation of the motor 190 and drive components 196. Controller 194 may include one or more processors. Controller 194 may further include memory in some embodiments.

Motor 190 is connected to the controller 194 and syringe pump components generally. Motor 190 may be included in the plunger driver assembly 114 in some embodiments. Motor 190 is the primary means for directing the drivetrain 196 (or drive components) to effect movement of the plunger driver assembly 114. Drivetrain 196 may be a set of drive components that are at least partially located in the housing 112 which are responsible for mechanically directing infusion of fluid from a syringe that has been operatively installed in pump 100.

The syringe pump system further includes either line power via a cord connected to the power receptacle 166 or via a connector in a rack that connects to the power receptacle 166. Battery 174 provides another alternate source of power to the infusion pump 100. In an embodiment, battery 174 is fully enclosed in the housing 112 beneath the rear battery panel 164.

Various electrical components and electrical circuitry 198 are located within the housing 112 that are required for relaying or carrying out commands to the controller 194 or within the system. Various outside devices may be connected to the syringe pump 100 as well through inputs, such as an Ethernet connector 168 or USB input port 170.

The speakers 128 are equipped to provide a full range of audio output including commands, alerts, and informative communications. Plunger driver head sensors 199 and other sensors are part of the system as well. Plunger driver sensors 199 can, for example, make various measurements for tasks such as characterizing syringes, detecting occlusions, and determining plunger position. Controller 194 utilizes information gained from these sensors 199 and other components to assist in communications and decision-making in set-up and operation of pump 100.

LVP

Referring to FIGS. 8-13, an example of a LVP 200 is shown. LVP 200 generally includes a user interface 210, housing 212, and assembly receptacle 213. Various other features of the LVP 200, including some that are internal or partially or fully obscured by the housing 212, will be later described with reference to the LVP system diagram of FIG. 14.

In general, significant portions of LVP 200 in FIGS. 8-14 and the syringe pump 100 described above and in FIGS. 1-7 are similar or identical. Accordingly, discussions of components having reference numerals in the "100's" in FIGS. 1-7 should generally be deemed to correspond to and apply to the similar components having corresponding reference numerals in the "200's" in FIGS. 8-14, unless otherwise distinguished in the following discussion (for example, the discussion of keypad 120 in FIG. 1 applies to keypad 220 in FIG. 8 as well).

Figure 8:
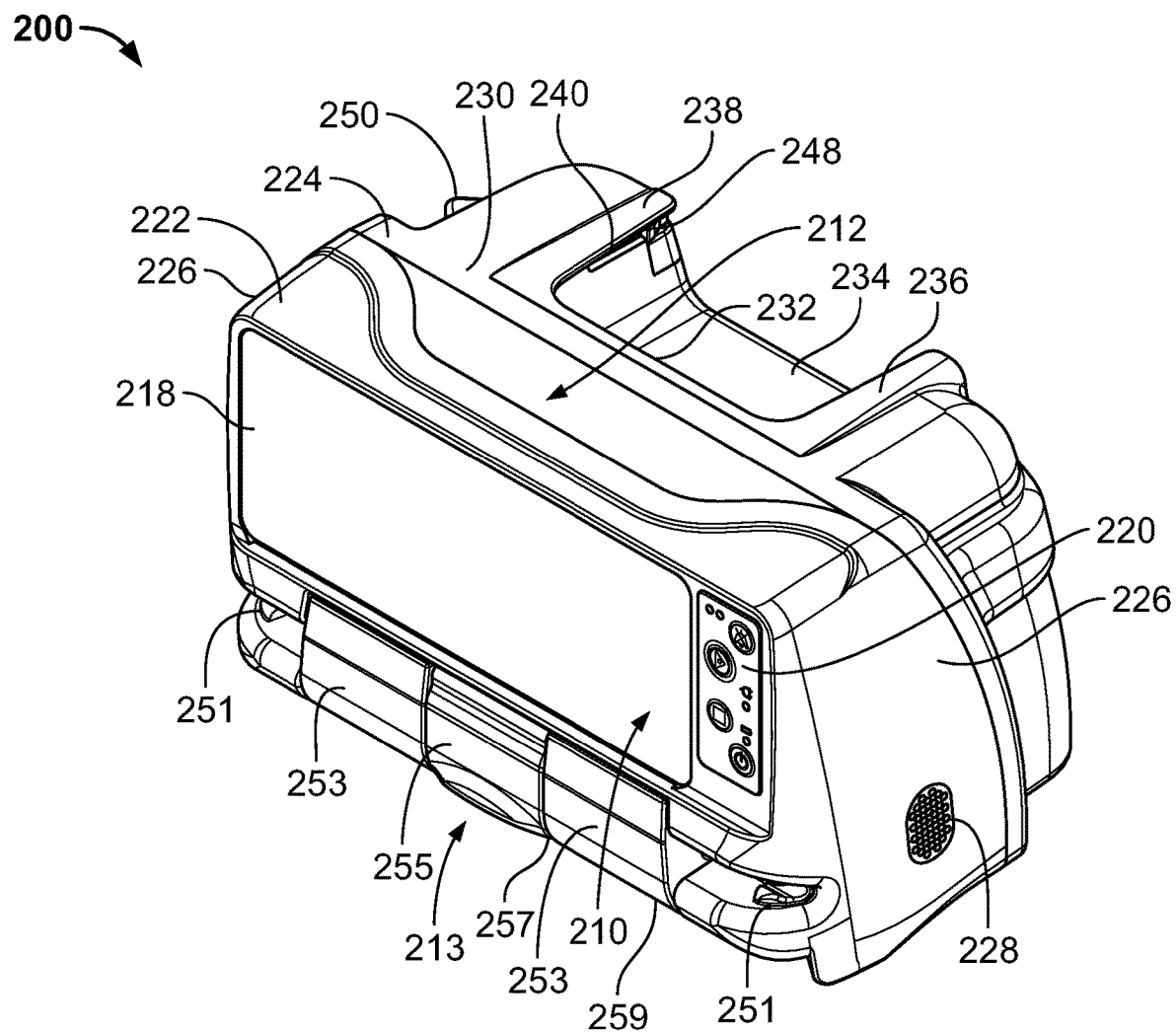
FIG. 8 is front perspective view of a LVP, according to an embodiment.

As seen in FIG. 8, user interface 210 generally includes a display screen 218 and a keypad 220. User interface 210, display screen 218 and keypad 220 respectively correspond to user interface 110, display screen 118 and keypad 120. A variety of configurations for touchscreen and mechanical buttons are contemplated.

The housing 212 corresponds to housing 112 and generally forms a protective shell surrounding the internal components of the LVP 200. In some embodiments, the user interface 210 may be considered part of the housing 212. The housing 212 can be characterized as generally comprising a front housing assembly 222 and a rear housing assembly 224.

Front housing assembly 222 generally surrounds the LCD display screen 218, keypad 220 and other components in the proximity of the user interface 210. Front housing assembly 222 is largely the same as the front housing assembly 122 of the syringe pump 100, however, the shape of the front housing assembly 222 around the assembly receptacle 213 and user interface 210 is shaped differently so that the features of the assembly receptacle 213 are appropriately accommodated.

Rear housing assembly 224 is generally consistent with rear housing assembly 124. Features on the rear housing assembly 224 include a handle 232, central recess 234, and a generally U-shaped retaining feature 236 defined in the top portion 230 of the housing 212. These features are analogous to those discussed with respect to the syringe pump 100 as well. The generally U-shaped upper lip portion 238 surrounding central recess 234 and receiving grooves 240 extend inwardly from rear face 242. This arrangement provides features for receiving a projection of another pump and gripping the U-shaped retaining features 236 as a handle 232.

As in the syringe pump 100, the handle 232 of the LVP 200 is integrated with housing 212 and is part of the generally U-shaped retaining feature 236. Similarly, generally U-shaped projection 252 is located on the bottom portion 254 of the housing 212 and is analogous to the generally U-shaped projection of the syringe pump 100. As in the configuration of syringe pump 100, U-shaped projection 252 is comprised of a forward portion 256 and rearward portions 258. The rearward portions 258 include a flange 260 and outwardly extending lip 262 which are sized to engage with retaining grooves 240 of another pump. Accordingly, LVPs 200 and syringe pumps 100 can be readily stacked and coupled with one another.

Figure 9:
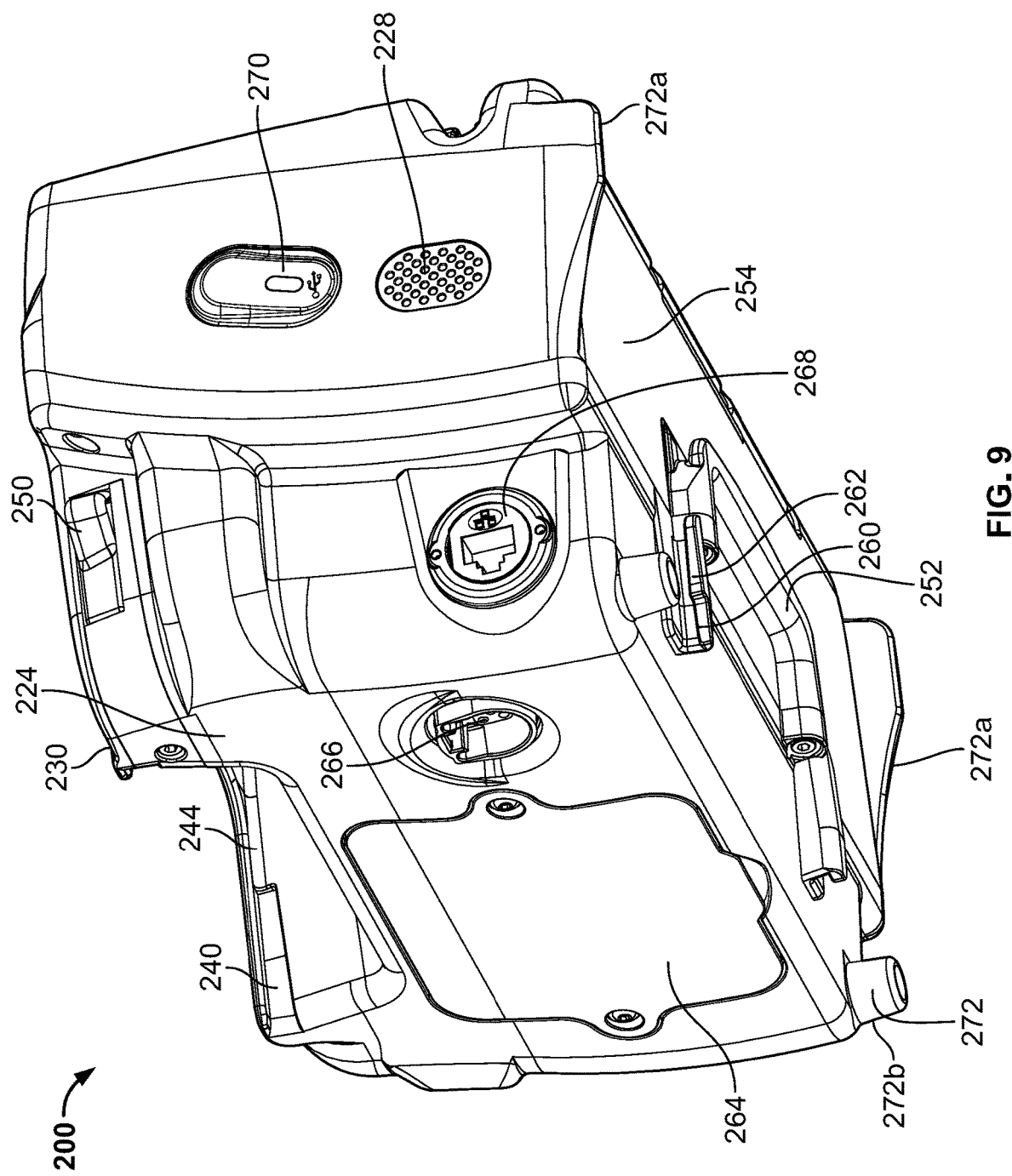
FIG. 9 is a rear perspective view of a LVP, according to an embodiment.

With particular reference to FIG. 9, features that can be seen on the rear face 224, sides 226, and bottom portion 254 of the housing 212 include: a battery door cover 264, power receptacle 266, Ethernet connector 268, USB port 270, and mounting feet 272. Each of these components correspond to analogous parts of syringe pump 100.

Also shown in FIGS. 8-13, is an assembly receptacle 213. Assembly receptacle 213 includes an elongate cavity extending across the front of the LVP 200. Assembly receptacle 213 is located directly below the display screen 218 of the user interface 210. Assembly receptacle 213 contains passages 251 out each end as well as a central passage through which an infusion line for carrying out patient infusion can extend through and be acted on. Further, assembly receptacle 213 includes features permitting a tubing frame assembly of the patient infusion line to be removably mounted and acted on by fingers of a peristaltic pumping mechanism.

The interior features of the assembly receptacle 213 are largely obstructed from view in FIGS. 8-13 by a hinged door 253. Door 253 further contains a centrally located latch lever 255 for securing the door 253 in the closed position depicted. When the LVP 200 is in use, the door 253 is first placed in an open orientation. A tubing frame assembly coupled to the infusion line is received by the assembly receptacle 213. This loading of the tubing frame assembly can be done via one-handed motion. Next, the door 253 can be rotated closed about hinges 257 (as illustrated in, for example, FIG. 13) at the bottom front edge 259 of the LVP 200. Door latch lever 255 can then be moved from an unlatched position to a latched position as shown in FIGS. 8-13. For purposes of this description, the operational details of the LVP components in the assembly receptacle 213 are not specifically discussed.

Figure 10:
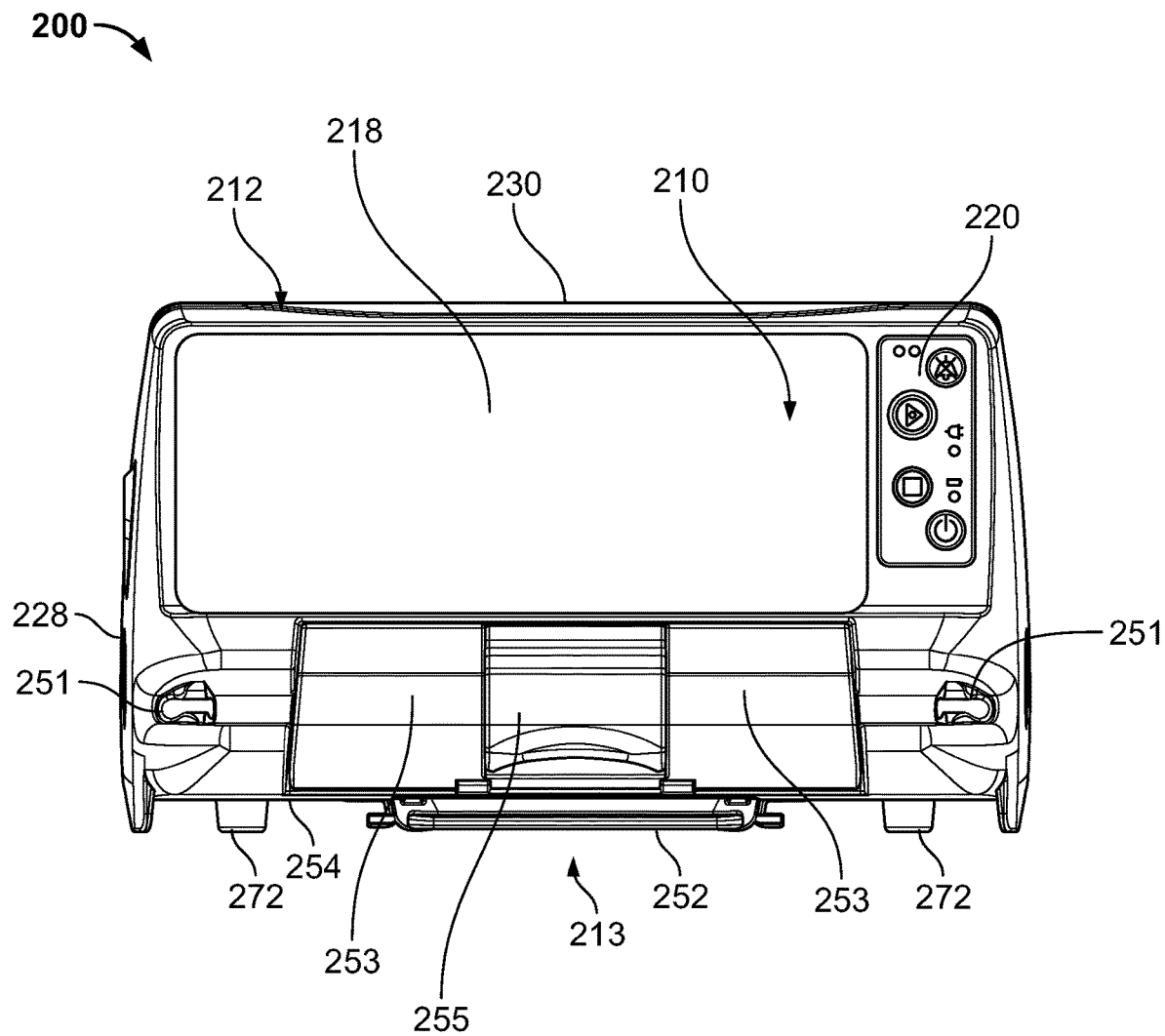
FIG. 10 is a front view of a LVP, according to an embodiment.
Figure 11:
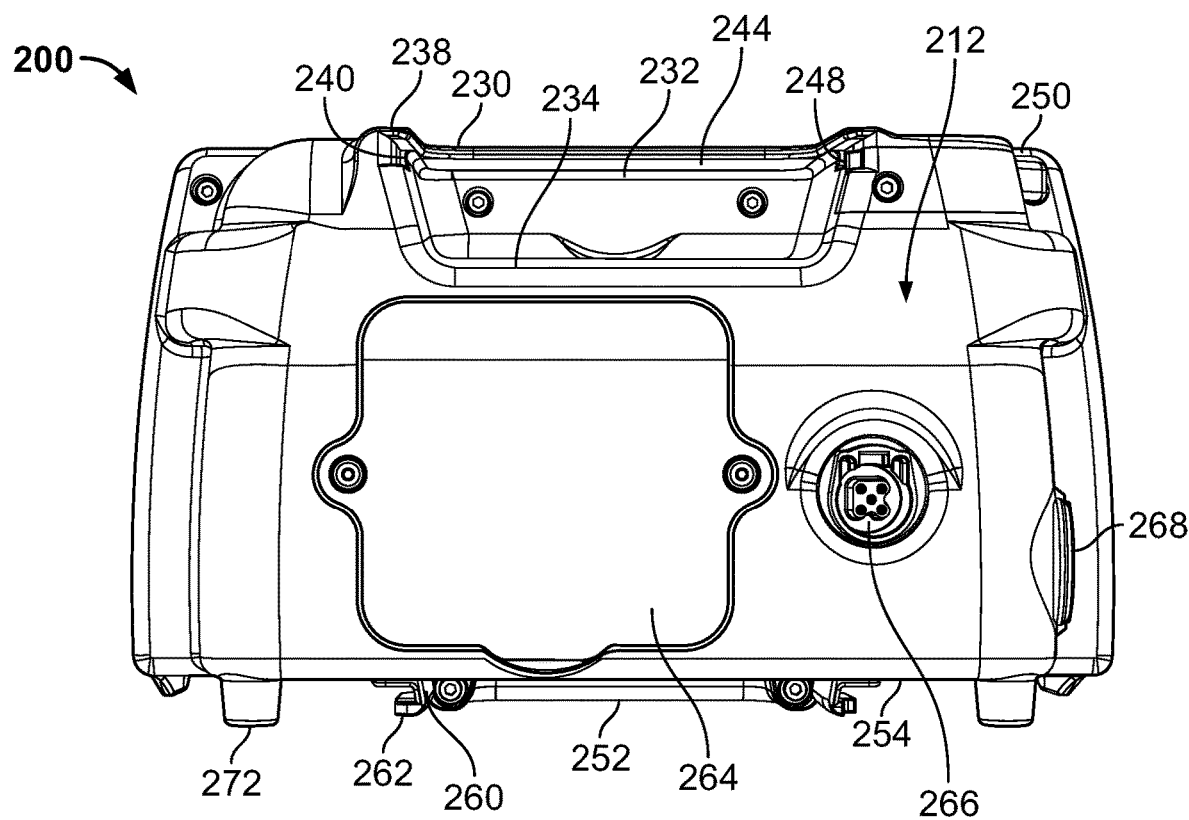
FIG. 11 is a rear view of a LVP, accordingly to an embodiment.
Figure 12:
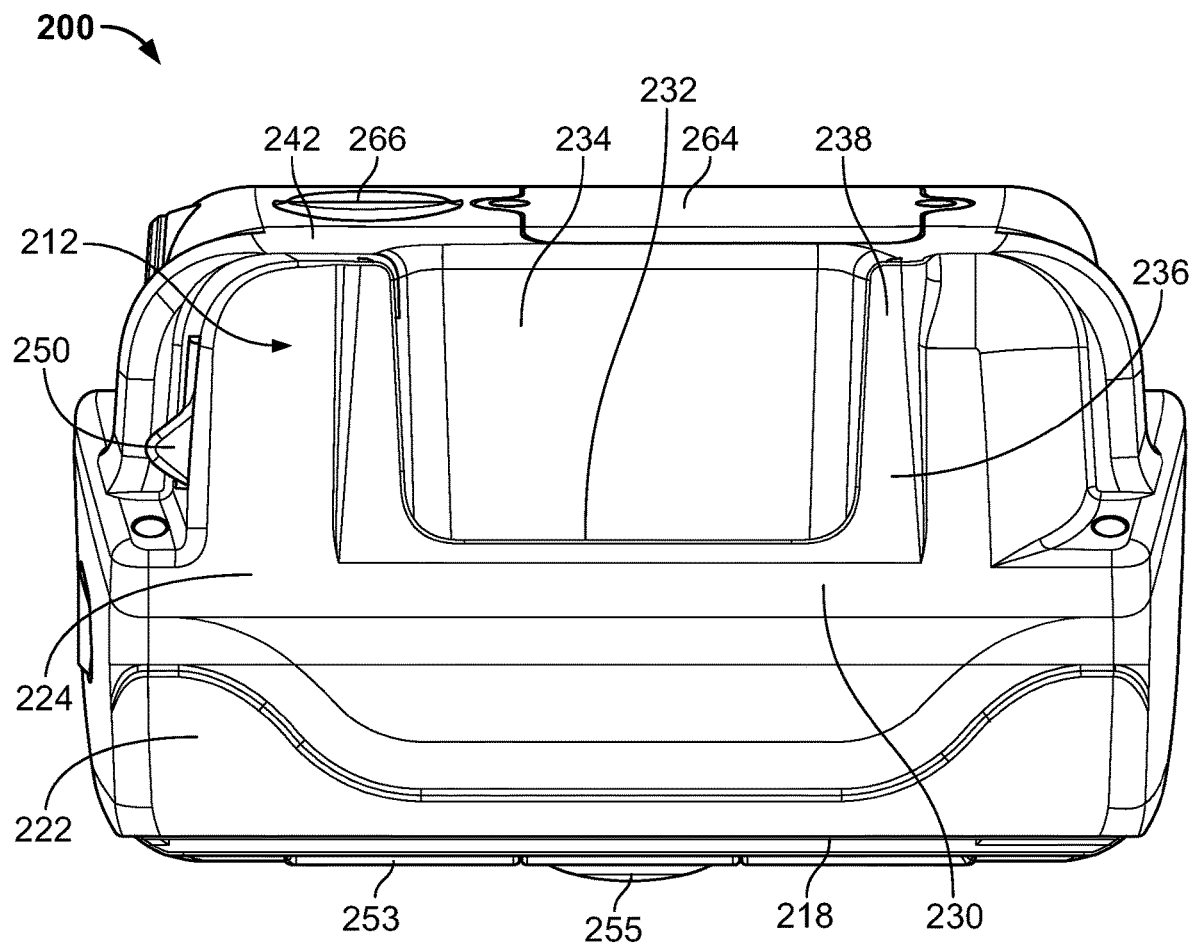
FIG. 12 is a top view of a LVP, according to an embodiment.
Figure 13:
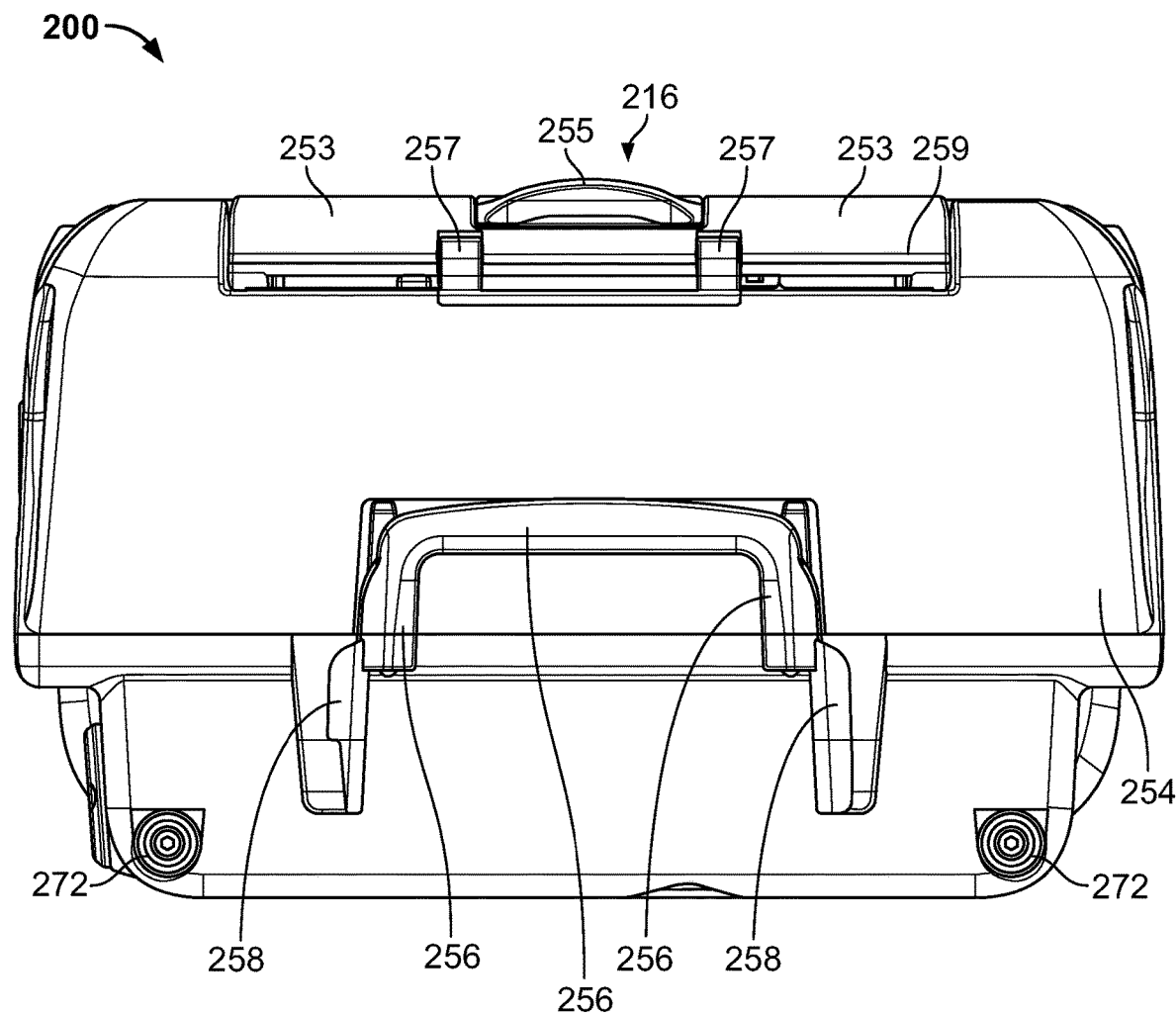
FIG. 13 is a bottom view of a LVP, according to an embodiment.

As depicted in, for example, FIG. 10, assembly receptacle 213 includes infusion line retention passages 251 at both ends. The retention passages 251 (or tube guides) provide a narrow segments in which an infusion line can pass. At any suitable time, which may be before or after door 253 is closed, upstream and downstream tubing (not illustrated in FIGS. 8-13) can be manually pressed into retention passages 251.

Various assemblies and methods for infusion system administration sets such as, for example, an aforementioned tubing frame assembly that can be removably secured in receptacle 213, are discussed in PCT App No. PCT/US2017/037929 of Adams et al., titled "Assemblies and Methods for Infusion Pump System Administration Sets", and published as WO 2017/218927 A1, which is hereby incorporated by reference.

Figure 14:
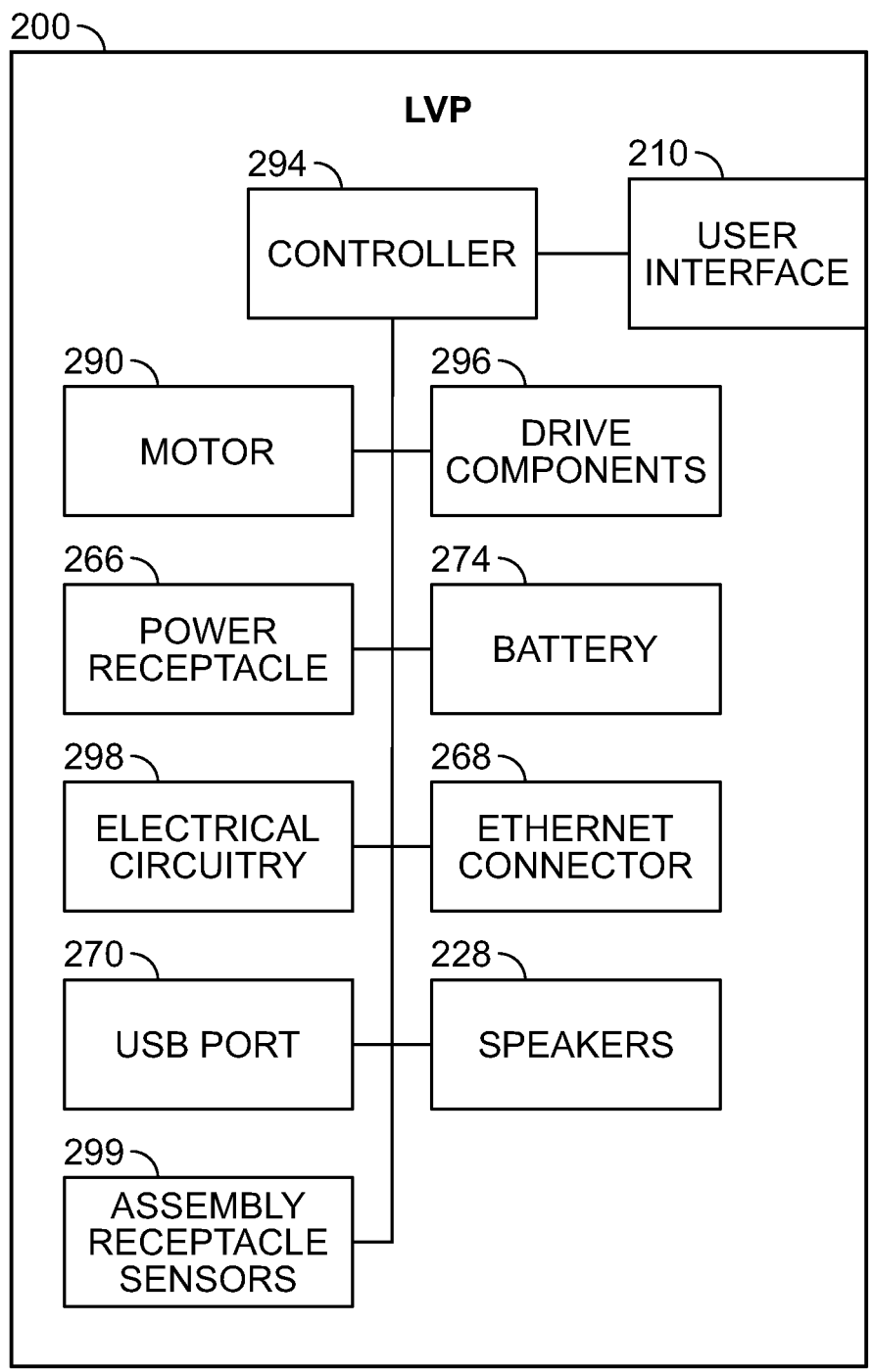
FIG. 14 is a general system diagram of a LVP, according to an embodiment.

FIG. 14 depicts an example of a general system diagram of the LVP 200, including some components that are partially or fully obscured by the housing 212. The system diagram shows a diagram of a LVP 200, including user interface 210, controller 294, motor 290, drive components 296, power receptacle 266, battery 274, electrical circuitry 298, Ethernet connector 268, USB input port 270, speakers 228, and assembly receptacle sensors 299.

As discussed above, the user interface 210 serves as a source of data input for the syringe LVP 200 from, for example, a medical clinician or pump programmer. Although not specifically illustrated in FIG. 14, it is to be appreciated and understood that user interface 210 may include a touchscreen display 218, keypad 220 or a combination of these or other user interface technologies.

In this example, controller 294 is connected to the user interface and is responsible for ensuring that the pump is controlled in the desired manner. Controller 294 may include one or more processors. Controller 294 may further include memory in some embodiments.

Motor 290 is connected to the controller and LVP components generally. Motor 290 can be a stepper motor in some embodiments. In this example, motor 290 is the primary means for directing the drive components 296 to effect movement of the fingers in the assembly receptacle 213 (as illustrated in, for example, FIG. 8) against the tubing.

The example of the LVP system in FIG. 14 further includes either line power, via a cord connected to the power receptacle 266 or, via a connection member in a rack that connects to the power receptacle. Battery 274 is another alternate source of power to the LVP 200. The battery 274 can be fully enclosed in the housing 212 beneath the rear battery door cover 264 (as depicted in FIG. 9, for example).

Referring again to FIG. 14, various electrical components and electrical circuitry 298 are located within the housing 212 for relaying or carrying out commands to the controller 294 or within the system. Various outside devices may be connected to the LVP 200 as well through inputs, such as an Ethernet connector 268 or USB port 270.

The speakers 228 are equipped to provide a full range of audio output including commands, alerts, and informative communications. Assembly receptacle sensors 299 and other sensors can be part of the system as well. Assembly receptacle sensors 299, for example, can make various measurements for tasks such as sensing information about the particular tubing frame assembly. This can include sensing the route of infusion for which a particular tubing frame assembly is used. Sensors can be optical sensors, RFID readers, etc. Controller 294 can utilize information gained from these sensors 299 and other components to assist in communications and decision-making in set-up and operation of pump 100.

As noted above, syringe pump 100 and LVP 200 make use of a plurality of individual FRUs that enable pump components to be readily upgraded or replaced. FRU components provide ease of pump manufacture as well as simplified maintenance and replacement. Various FRU configurations contemplated herein can be interchangeable and common to both types of infusion pumps discussed. In general, FRUs can be categorized into three groups: wear components (components that will need to be replaced due to breakage or end-of-life, etc.); faster moving technology (communications, WiFi, Bluetooth®, USB, the display); and functionality upgrades (syringe security, PCA, TCI, etc.). FRUs can be interchanged between categories at times as well by virtue of these being modules with interfaces. For example, to improve the performance of a wear component, a user might upgrade the functionality. E.g., a pumping mechanism that does not meet breakage or wear component requirements could be "upgraded" by higher performance or added feature FRUs—ones that have the desired capabilities to essentially replace the previous wear component. In a pump, a higher-performance FRU can be recognized by the pump and the pump's operating parameters can be adjusted automatically to be compatible with the newly installed FRU. Additionally, the pump would have knowledge of its configuration and therefore it would essentially report back its own configuration for logging into, e.g., a DMR (Device Master Record).

Figure 15:
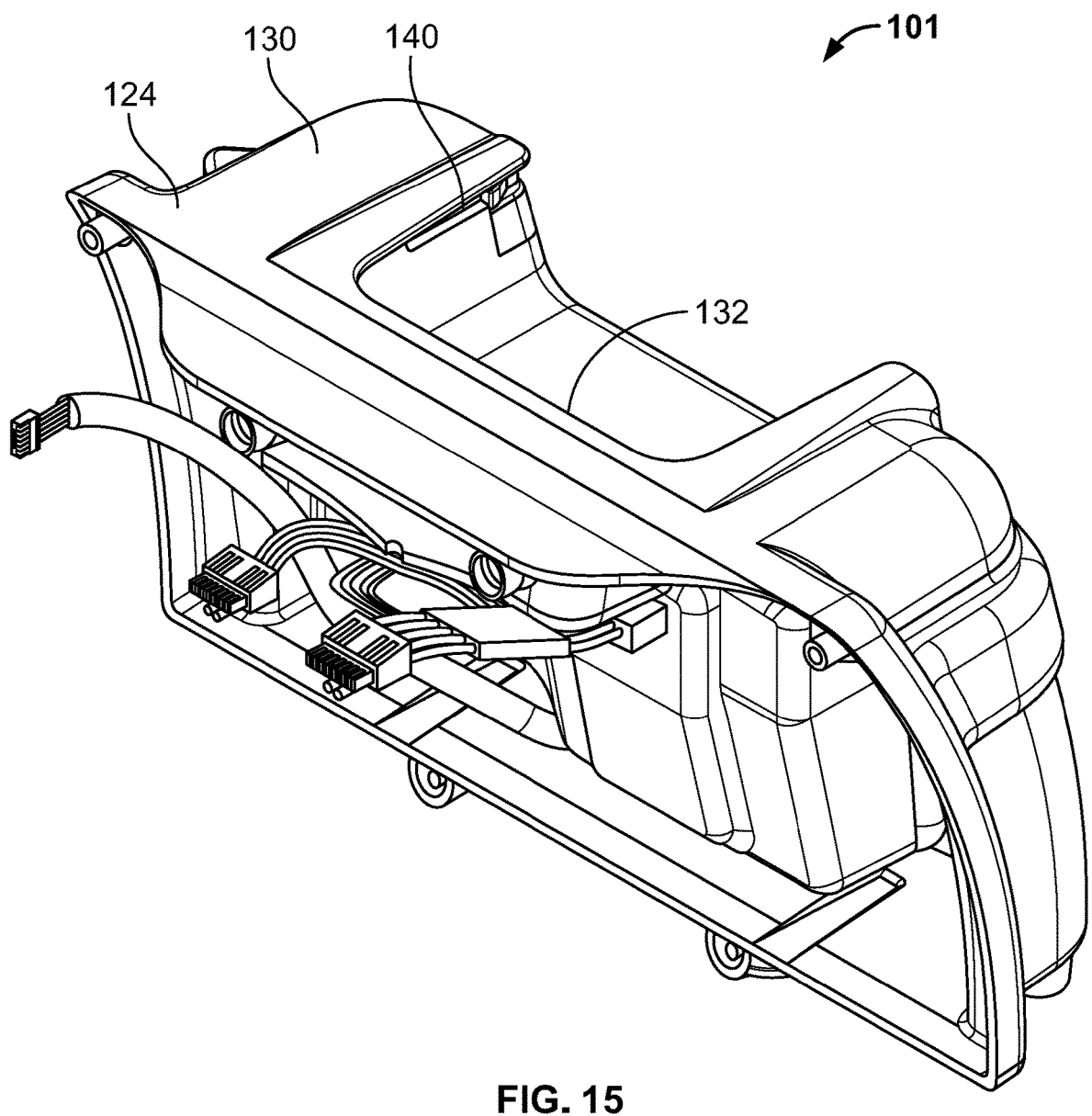
FIG. 15 is a perspective view of an example of an FRU comprising a rear housing portion for a syringe pump or LVP, according to an embodiment.

In one example, both syringe pump 100 and LVP 200 have a common FRU comprising the rear portion of the pumps. This common FRU includes significant portions of the housing and rear components for both types of infusion pumps discussed. This component is shown as FRU 101 in FIG. 15. and can be understood from corresponding reference numerals and parts of FIGS. 1-14 as well. Specifically, FRU 101 largely includes rear housing assembly 124 or 224 for an infusion pump. The rear housing 124 or 224 includes a top portion 130 or 230 and part of bottom portion 154 or 254. The top portion 130 or 230 has an integrally formed handle structure 132 or 232 and a set of receiving grooves 140 or 240. The bottom portion 154 or 254 has a projection 152 or 252 for releasable coupling with receiving grooves (such as 140 or 240) in another rear housing. The rear housing 124 or 224 can include a power receptacle 166 or 266 and an Ethernet connector 168 or 268. The rear housing 124 or 224 interchangeably couples with a set of infusion pump system components (such as a plunger driver assembly 114 and syringe receptacle 116 or LVP motor and drive components and assembly receptacle 213), a control system (such as controller 194 or 294), and a display of either a LVP or a syringe pump (such as display screen 118 or 218).

In some embodiments, FRUs can include components or groups of components of the pump. Examples of such FRUs can include: a rear housing assembly; an LVP front housing with motor, pump, display and keypad; a syringe front housing with display and keypad; a battery pack with gas gauge; a power supply; wireless components; a PCB BOARD assembly; a LVP door; a syringe drive; and a syringe plunger head.

In some embodiments, FRUs can include battery pack modules (additional, supplemental, or standby). Similarly, in some embodiments, FRU's can include battery charging or power modules (possibly incorporating or interfacing with portable solar, wind, or mechanical crank-type generators). Interfaces to off-the-shelf batteries for military use can be provided in some embodiments. In certain cases, a battery charging or power module can interface with one or more pumps that are "connected". For example, a pump and a headless pump, in a stack could all interface with a battery charging or power module.

In some embodiments, FRUs can include alarm modules (both visual and/or audible). Specifically an alarm module can interface with one or more pumps that are "connected". For example, a pump and a headless pump, in a stack could all interface with an alarm module.

In some embodiments, FRUs can include: PCA modules; syringe security devices (such as a lockbox); a communications module; or a user authentication module (such as one using biometric inputs, of fingerprints, voice, facial recognition, etc.) that can unlock an entire connected stack.

In some embodiments, FRUs of power and communication relate to alternatives to or proxies for a rack. In some embodiments, FRUs having Bluetooth® or Wifi are contemplated. In some embodiments, the FRUs can be in a daisy chain of communication (wired or wireless) and/or power. In some cases, FRUs include power selector or adapter modules. For example, modules for adaptation to local (unique) power sources or power sources that are commonly used for or in other devices (AC/DC power). In various embodiments, FRUs can be locked.

In other contemplated embodiments, the pumps themselves can be FRUs. For example, this can be the case in a collective pumping arrangement comprising a syringe pump, an LVP and a headless syringe. In some embodiments, an FRU can copy the programming of a device that has failed. See PCT App. No. PCT/US2017/042633 of Diez et al., titled "Cloning Medical Device Configurations", and published as WO 2018/022355 A1, which is hereby incorporated by reference.

Figure 16A:
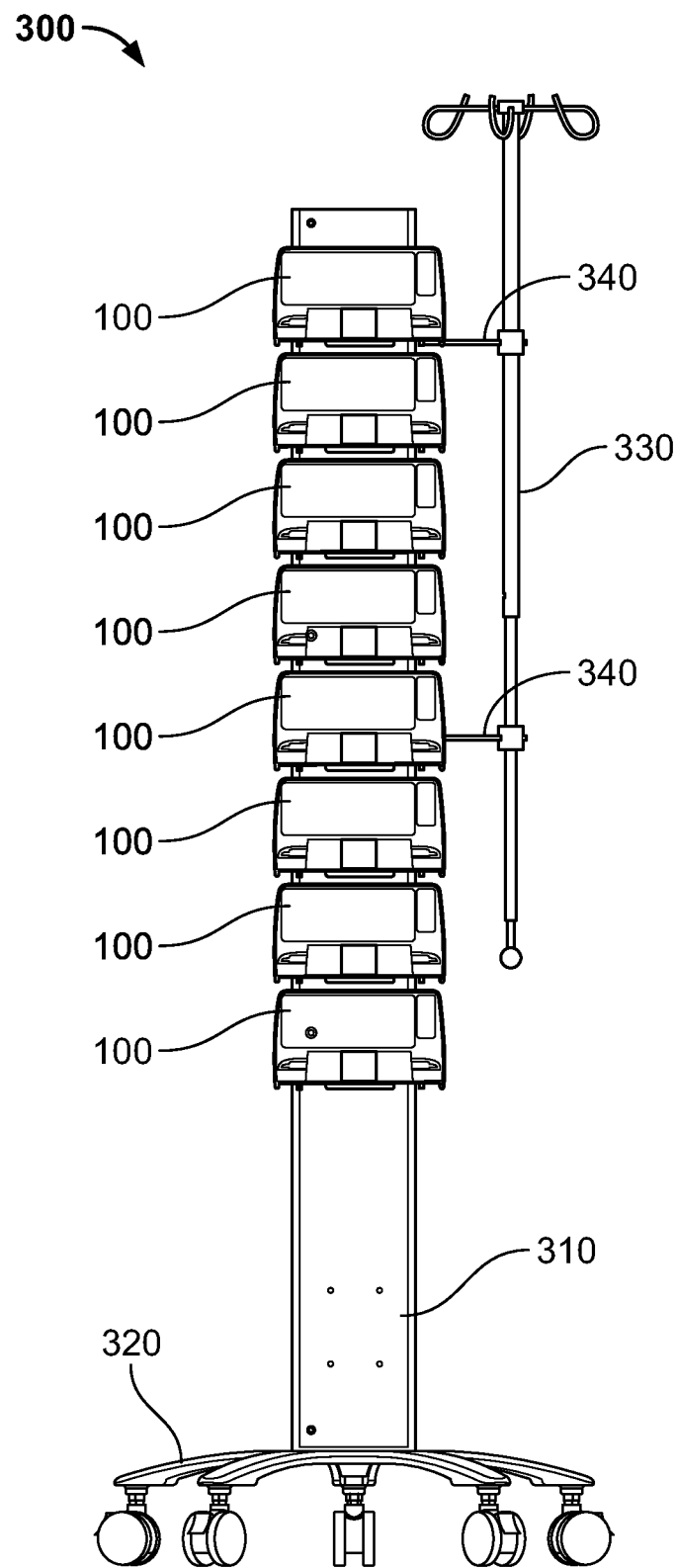
FIG. 16A is a perspective view of a racking arrangement of infusion pumps, according to an embodiment.
Figure 16B:
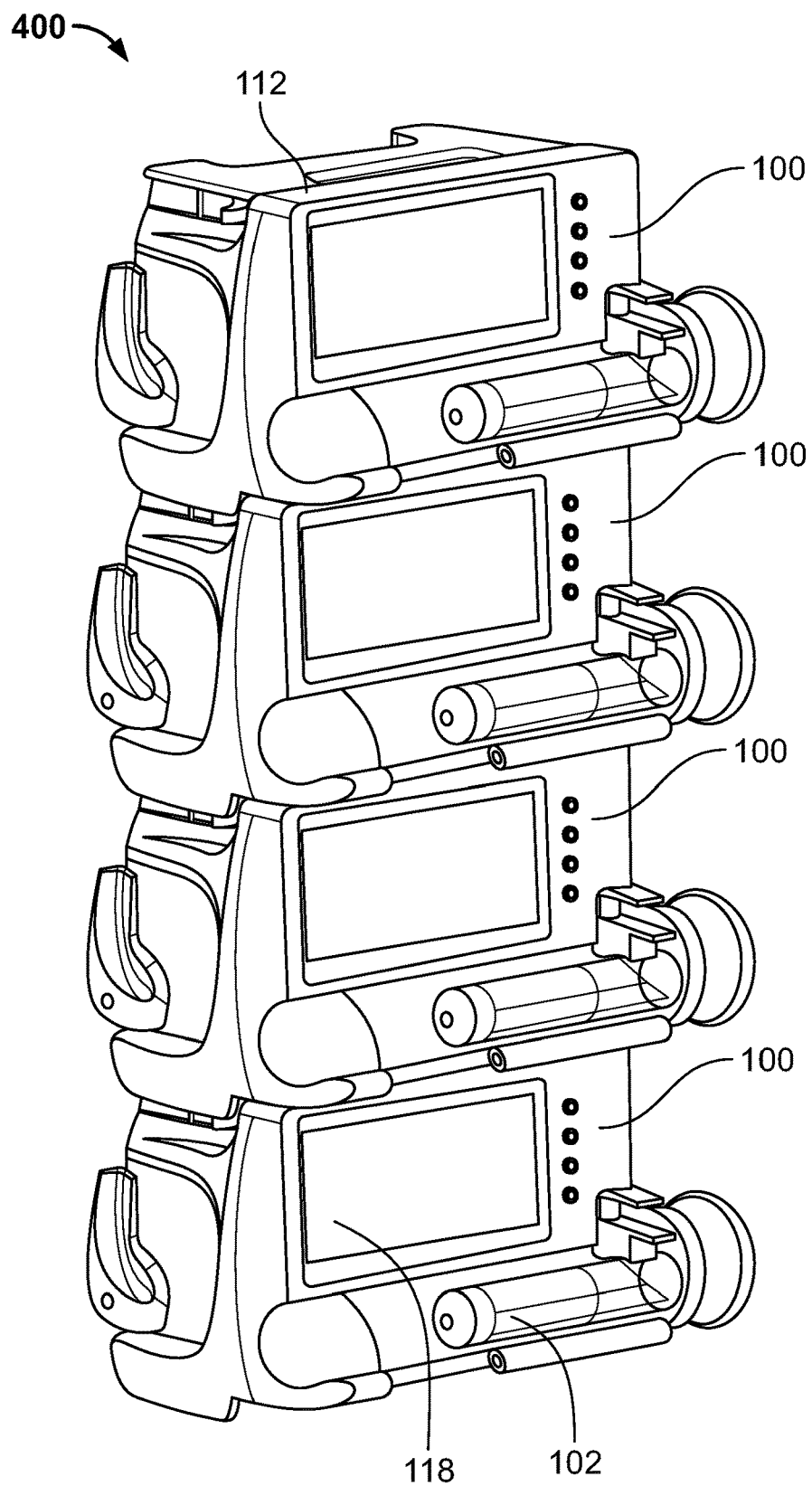
FIG. 16B is a perspective view of a stacking arrangement of infusion pumps, according to an embodiment.

Referring to FIGS. 16A and 16B, infusion pump arrangements are shown which depict the racking and stacking capabilities of the pumps. Specifically, FIG. 16A depicts a pole mounted arrangement 300 in which a plurality of syringe pumps 100 are mounted on a movable rack 310. Rack 310 is designed to hold up to eight infusion pumps 100, as depicted, in some embodiments. Rack 310 has a wide wheeled base with legs 320 which aids in preventing the rack from tipping. Further, an IV pole 330, is attached via arms 340 extending from the side of the rack 310. The IV pole 330 is located above a leg 320 of the rack 310 so that the weight of any bag(s) of mounted fluid or infusate, such as an IV bag, will be supported and will not cause instability to the rack 310. In some embodiments, rack 310 can be further advantageous as it can provide an AC power supply, space management, and a consolidated Ethernet connection.

Rack 310 permits the individual installation and removal of infusion pumps, such as syringe pumps 100. This individualized mounting capability means that a suitable syringe pump 100 or other suitable infusion pump can be readily installed or removed from a group of such pumps. This flexibility is particularly advantageous for troubleshooting and reconfiguring groups of infusion pumps.

The vertically grouped arrangement of the racked arrangement 300 in FIG. 16A can be analogous to the stacked arrangement 400 of FIG. 16B as well. Specifically, in this example of FIG. 16B, syringe pumps 100 can be seen stacked directly above or below each other, vertically. This type of stacking may utilize a pole mount, in some embodiments, for example. When the top syringe pump 100 is secured in place, for example, a subsequent syringe pump 100 can be secured below it by attachment features integrated into the syringe pump housing 112 of both pumps. Specifically, and as aforedescribed, the generally U-shaped projection 152 on the bottom of the top syringe pump 100 permits the receiving grooves 140 of the generally U-shaped retaining feature 136 of the below syringe pump 100 to be slid over the outwardly extending lip 162. The U-shaped retaining feature 136 is slid until the forward portion 156 of the U-shaped projection 152 abuts underneath the upper lip portion 138 of the below syringe pump 100. A feature of this stacked arrangement of syringe pumps 100 is that each user interface display screen 118, as well as corresponding syringes 102, can be readily viewed at the same time. This permits a medical practitioner the ability to quickly see the status of all the syringe pumps at one glance, even if done from across a room.

Although FIGS. 16A and 16B show syringe pumps 100 in racked and stacked arrangements, other types of infusion pumps should be understood to be capable of being racked and stacked in this manner, as well, such as LVPs 200. Accordingly, racks and stacks of either all syringe pumps 100, all LVPs 200, or a mix of different kinds of pumps racked or stacked together are possible.

Figure 17:
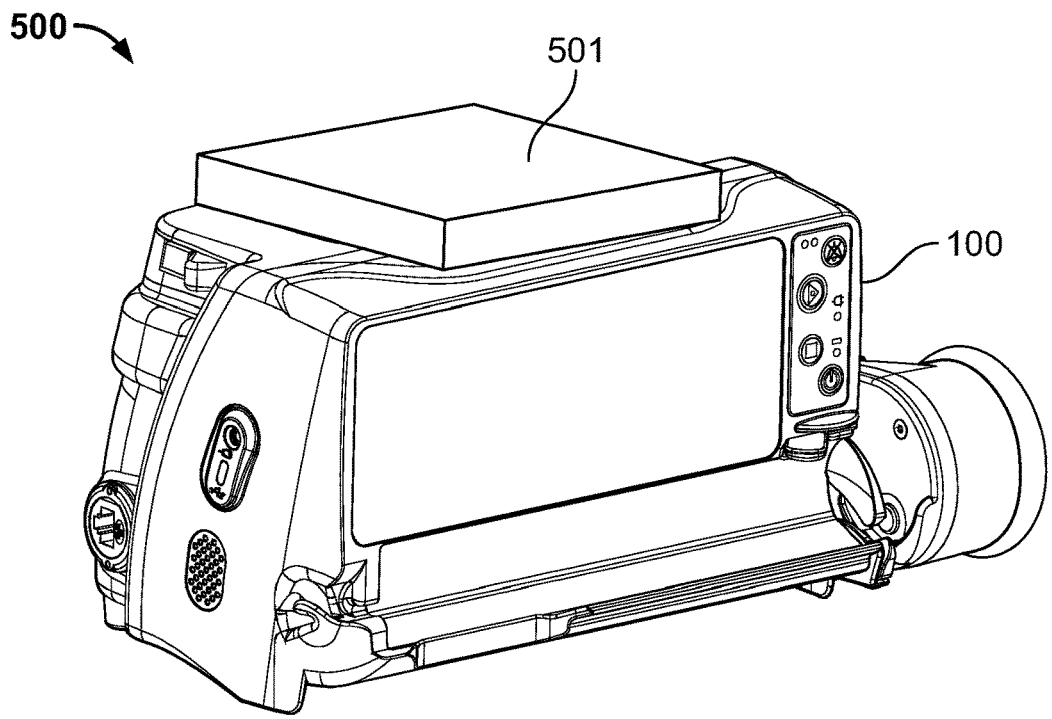
FIG. 17 is a perspective view of an infusion pump arrangement having an external backup battery pack, according to an embodiment.

Referring to FIG. 17, a perspective view is shown of an infusion pump configuration 500 in which an external backup battery pack 501 is attached to a syringe pump 100. An external backup battery pack 501 may be used in cases where access to AC power is limited. For example, in more remote regions or in transport vehicles, having a group of battery power supplies can provide the flexibility needed to run infusion pumps in nearly any location for extended periods of time. The external backup battery pack 501 contemplated can have a cord which plugs into the power receptacle 166 in the back of the housing 112 to supply power to the syringe pump 100. The external backup battery pack 501 can also have a generally U-shaped projection of the battery pack 501 on its bottom surface similar to the generally U-shaped projections 152 and 252 on the bottom of the infusion pumps 100 and 200 described herein. Accordingly, this generally U-shaped projection is able to mate with the generally U-shaped retaining feature 136 or 236 on the top of the pump 100 or 200. This arrangement provides a secure and durable coupling for the pump 100 or 200 and its power supply. Moreover, once external backup battery pack 501 runs low on power, another similar unit can simply replace it and likewise attach to the top portion of the syringe pump 100.

Figure 18:
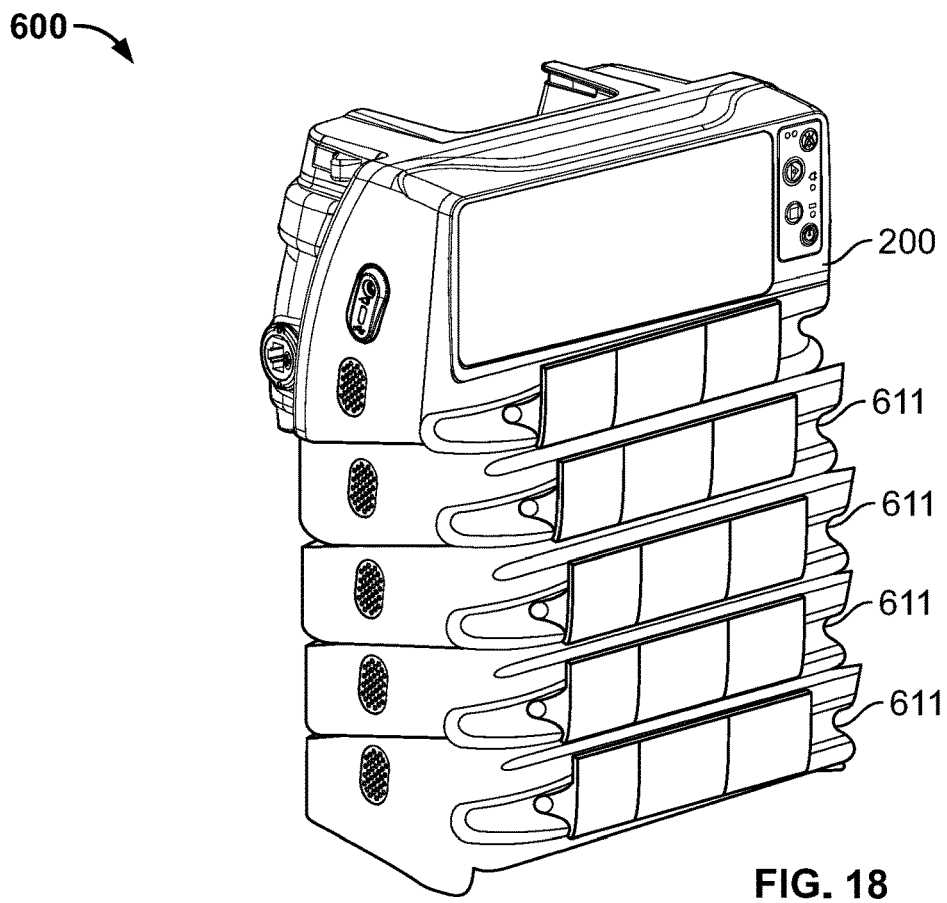
FIG. 18 is a perspective view of a stacking arrangement of a LVP with other "headless" LVPs, according to an embodiment.

FIG. 18 depicts an embodiment of an infusion pump configuration 600, including a set of infusion pumps including a LVP 200 coupled to a set of stacked, "headless" LVPs 611. In general, LVP 200 depicts an LVP similar to those described in FIGS. 8-14. This LVP 200 is shown in a stacked arrangement with other "headless" LVPs 611. These LVPs 611 are "headless" in the sense that they do not contain the user interface 210 of LVP 200 and are much more compact in size. These headless LVPs 611 are made possible when a stacked arrangement (or racked, if on a rack) is constructed and operatively coupled in communication which can rely on one user interface 210 to control pumping operations of a stacked or (racked) set of infusion pumps. Constructing such "headless" LVPs without including relatively more expensive user interface components on each pump can provide a significant cost savings to pump manufacturing. In an embodiment, "headless" pumps can communicate with each other via Bluetooth® or other wireless communication. "Headless" pumps can also be, additionally or alternatively, wired to each other and may communicate via USB or Ethernet ports, for example.

Headless LVPs 611 may each include a generally U-shaped retaining feature 236 on their top surfaces and a generally U-shaped projection 252 on the bottom surface similar to the ones described for the LVPs 200. Accordingly the pumps can be readily coupled with so-called "tongue-and-groove" arrangement similar to the arrangements 300 and 400 in FIGS. 16A and 16B. Further, "headless" pumps are not limited to LVPs. Syringe pumps 100 can also be provided as "headless" infusion pumps in which no user interface is contained on certain syringe pumps 100 in a pump stack or rack.

Other ease of use features are also contemplated by this disclosure. For example, in some embodiments, all pump components with which a user is intended to interface are specially color coded. In the case of the example of syringe pump 100 herein, each of the areas for user interaction are visually color-coded blue. Accordingly, the bumper 184, trigger 186, keypad 120, barrel clamp lever 192, USB port 170, Ethernet connector 168, catch 148 and pump latch button 150 would be colored blue. In the case of the LVP 200, the latch lever 255, keypad 220, USB port 270, Ethernet connector 268, catch 248 and pump latch button 250 would be colored blue.

Throughout this disclosure and figures, generally U-shaped retaining feature 136, generally U-shaped retaining feature 236, generally U-shaped projection 152, generally U-shaped projection 252, and other features described as "generally U-shaped" should be interpreted in a largely non-limiting manner and can also be alternatively and/or interchangeably referred to understood as simply being "U-shaped". Although the components referenced are largely understood based on their depiction from a top or bottom perspective, the "U-shaped" and "generally U-shaped" terminology should be interpreted in a largely non-limiting way. For example, the description can be understood to include one continuous largely semicircular shape or a shape having a base with two side members extending therefrom. The term "U-shape" can include base and side components having rounded or squared intersections. The side components can be disposed in parallel, converging or diverging orientations. In some embodiments, a "generally U-shaped" component is broad enough to include side members that meet at a single base location to form a "V". Other configurations are possible as well. Accordingly, corresponding claim terms should be interpreted in a corresponding, broadly construed manner.

Various embodiments of systems, devices, and methods have been described herein. These embodiments are given only by way of example and are not intended to limit the scope of the claimed subject matter. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed subject matter.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:
1. An infusion pump, comprising:
 a housing enabling selective stacked attachment with other infusion pumps, the housing including:
  a front side;
  a rear side;
  a top portion comprising a generally U-shaped retaining feature having:
   an upper lip portion extending inwardly toward a central recess, the upper lip portion extending around the retaining feature;
   a handle formed in an outer surface of the housing and partially defined by the central recess;
   a narrowed section of housing; and
   a pair of receiving grooves oriented underneath the upper lip portion, each receiving groove extending between the narrowed section of the housing to the rear side;
  a bottom portion comprising a generally U-shaped projection having:
   a forward portion arranged in the middle of the generally U-shaped projection; and a pair of rearward portions each including a flange and an outwardly extending lip, each rearward portion configured to be slidingly inserted into a receiving groove and abut against a narrowed section of housing of a corresponding other infusion pump;

a user interface providing a front side to the housing that receives commands regarding infusion pump operation;

a motor and a set of drive components, at least partially located within the housing, that mechanically direct infusion of an infusate; and a controller located within the housing that controls operation of the motor and the set of drive components.

2. The infusion pump of claim 1, wherein the infusion pump is a syringe pump.

3. The infusion pump of claim 1, wherein the infusion pump is an LVP pump.

4. The infusion pump of claim 1, wherein the user interface includes both a touchscreen and a keypad control.

5. The infusion pump of claim 1, wherein the housing includes an external battery pack having a projection that removeably mates within the generally U-shaped retaining feature.

6. A syringe pump, comprising:

a syringe receptacle configured to receive a syringe of an infusate;

a syringe plunger driver assembly located adjacent the syringe receptacle, that directs the infusate from the syringe to a patient based on movement against a plunger of the syringe;

a housing coupled with the syringe receptacle, the housing including:
a front side including a GUI display for controlling the syringe pump;
a rear side;
a top portion comprising a retaining feature having:
an upper lip portion extending inwardly toward a central recess, the upper lip portion extending around the retaining feature;
a handle formed in an outer surface of the housing and partially defined by the central recess;
a narrowed section of housing; and
a pair of receiving grooves oriented underneath the upper lip portion, each receiving groove extending between the narrowed section of the housing to the rear side; and
a bottom portion comprising a projection having:
a forward portion arranged in the middle of the projection; and
a pair of rearward portions each including a flange and an outwardly extending lip, each rearward portion configured to be slidingly inserted into a receiving groove and abut against a narrowed section of housing of a corresponding other infusion pump,
wherein each of the retaining feature and the projection are arranged within a boundary defined by the rear side and the GUI display on the front side,
wherein the syringe receptacle is located on the front side of the housing vertically adjacent the GUI display in non-overlapping alignment, the housing configured such that both the syringe in the syringe receptacle and the entire GUI display are visible on the front side of the housing.

7. The syringe pump of claim 6, wherein the syringe receptacle is located beneath the GUI display.

8. The syringe pump of claim 6, wherein the GUI display is a touchscreen.

9. The syringe pump of claim 6, wherein four lines of text are displayable on the GUI at the same time.

10. The syringe pump of claim 6, wherein the syringe pump is configured for one-handed operation.

11. An infusion pump assembly, comprising:

a first infusion pump having a housing and a user interface with a display screen, the housing including:
a front side; and
a bottom portion comprising a generally U-shaped projection having:
a forward portion arranged in the middle of the generally U-shaped projection; and
a pair of rearward portions each including a flange and an outwardly extending lip; and
a headless infusion pump having no display screen, the headless infusion pump including:
a rear side;
a top portion comprising a generally U-shaped retaining feature having:
an upper lip portion extending inwardly toward a central recess, the upper lip portion extending around the retaining feature;
a handle formed in an outer surface of the housing and partially defined by the central recess;
a narrowed section of housing; and
a pair of receiving grooves oriented underneath the upper lip portion, each receiving groove extending between the narrowed section of the housing to the rear side;
wherein the headless infusion pump is configured to be releasably slidingly coupled to the housing of the first infusion pump by tongue and groove attachment, each rearward portion of the first infusion pump configured to be slidingly inserted into each receiving groove and abut against the narrowed section of housing of the headless infusion pump.

12. The infusion pump assembly of claim 11, further including a plurality of headless infusion pumps.

13. The infusion pump assembly of claim 12, wherein the plurality of headless infusion pumps contain both a LVP and a syringe pump.

14. The infusion pump assembly of claim 12, wherein the plurality of headless infusion pumps communicate with one another via Bluetooth.

15. The infusion pump assembly of claim 11, wherein the first infusion pump is a syringe pump.

16. The infusion pump assembly of claim 11, wherein the first infusion pump is a LVP.

17. A field replaceable unit for infusion pumps, comprising:

a rear housing for an infusion pump including:
a rear side;
a top portion comprising a retention feature having:
an upper lip portion extending inwardly toward a central recess, the upper lip portion extending around the retaining feature;
a handle formed in an outer surface of the housing and partially defined by the central recess;
a narrowed section of housing; and
a set of grooves oriented underneath the upper lip portion, each receiving groove extending between the narrowed section of the housing to the rear side;
a bottom portion comprising a projection having:

a pair of rearward portions each including a flange and an outwardly extending lip, each rearward portion configured to be slidingly inserted into a receiving groove and abut against a narrowed section of a corresponding other field replaceable unit for infusion pump; and wherein the rear housing interchangeably couples with a set of medication delivery components, a control system, and a display of different types of infusion pumps, including a LVP and a syringe pump.

18. The field replaceable unit for infusion pumps of claim 17, wherein the rear housing interchangeably couples with a set of medication delivery components, a control system, and a display of a patient-controlled analgesia pump.

* * * * *